(12) United States Patent
Eaton et al.

(10) Patent No.: US 9,839,391 B2
(45) Date of Patent: Dec. 12, 2017

(54) PERFORMING AND MONITORING DRUG DELIVERY

(71) Applicant: EYE DROP IMAGING TECHNOLOGY, LLC, Fort Myers, FL (US)

(72) Inventors: Alexander M. Eaton, Fort Myers, FL (US); Gabriel Gordon, Santa Barbara, CA (US); Guangjun Gao, Fort Myers, FL (US)

(73) Assignee: EYE DROP IMAGING TECHNOLOGY, LLC, Fort Myers, FL (US)

( * ) Notice: Subject to any disclaimer, the term of this patent is extended or adjusted under 35 U.S.C. 154(b) by 320 days.

(21) Appl. No.: 14/438,716

(22) PCT Filed: Nov. 6, 2013

(86) PCT No.: PCT/US2013/068654
§ 371 (c)(1),
(2) Date: Apr. 27, 2015

(87) PCT Pub. No.: WO2014/081570
PCT Pub. Date: May 30, 2014

(65) Prior Publication Data
US 2015/0289805 A1 Oct. 15, 2015

Related U.S. Application Data

(60) Provisional application No. 61/723,376, filed on Nov. 7, 2012, provisional application No. 61/806,471, filed (Continued)

(51) Int. Cl.
*G06K 9/00* (2006.01)
*A61B 5/00* (2006.01)
(Continued)

(52) U.S. Cl.
CPC .......... *A61B 5/4833* (2013.01); *A61B 90/361* (2016.02); *A61F 9/0008* (2013.01);
(Continued)

(58) Field of Classification Search
CPC .......... A61F 9/0008; A61M 2205/3306; A61B 2576/00; A61B 5/4833; A61B 90/361; A61B 2017/00831; G06F 19/3456
(Continued)

(56) References Cited

U.S. PATENT DOCUMENTS 6,398,766 B1 * 6/2002 Branch ............... A61H 35/02
604/294
2004/0091158 A1 * 5/2004 Miled ................. H04N 19/63
382/236
(Continued)

FOREIGN PATENT DOCUMENTS

WO 2009148345 A2 12/2009
WO WO 2009/0148345 * 12/2009 .......... A61F 9/0026
WO 2011064775 A1 6/2011

*Primary Examiner* — Amara Abdi
(74) *Attorney, Agent, or Firm* — Yakov S. Sidorin; Quarles & Brady LLP

(57) ABSTRACT

An opto-mechanical system for operation with a container containing a fluid to be administered in an eye or a container such as a syringe for example to administer an insulin injection. The mount of the system is equipped with an optical system and a processing/recording means configured to receive optical data, from light (visual or infra-red) reflected by an area in the vicinity of the eye, which data represents temporal and spatial characteristics of a process of administering drops of the fluid from the container into the eye. Image analysis software or human observation may be used to analyze the recorded images.

20 Claims, 17 Drawing Sheets

Related U.S. Application Data on Mar. 29, 2013, provisional application No. 61/808,425, filed on Apr. 4, 2013, provisional application No. 61/835,291, filed on Jun. 14, 2013.

(51) Int. Cl.
| | | |
|---|---|---|
| *A61F 9/00* | (2006.01) | |
| *G06F 19/00* | (2011.01) | |
| *A61B 90/00* | (2016.01) | |

(52) U.S. Cl.
CPC ...... *G06F 19/3456* (2013.01); *A61B 2576/00* (2013.01); *A61M 2205/3306* (2013.01)

(58) Field of Classification Search
USPC .................. 604/290, 295, 118; 382/128–132
See application file for complete search history.

(56) References Cited

U.S. PATENT DOCUMENTS

| | | | | |
|---|---|---|---|---|
| 2006/0173425 A1* | 8/2006 | Meierhoefer | ......... | A61F 9/0026 604/300 |
| 2010/0316292 A1* | 12/2010 | O'Hara | ................ | G06K 9/0063 382/168 |
| 2012/0143152 A1* | 6/2012 | Hunter | ................ | A61B 5/0059 604/298 |
| 2013/0018256 A1* | 1/2013 | Kislev | ................ | A61B 5/0084 600/431 |

\* cited by examiner

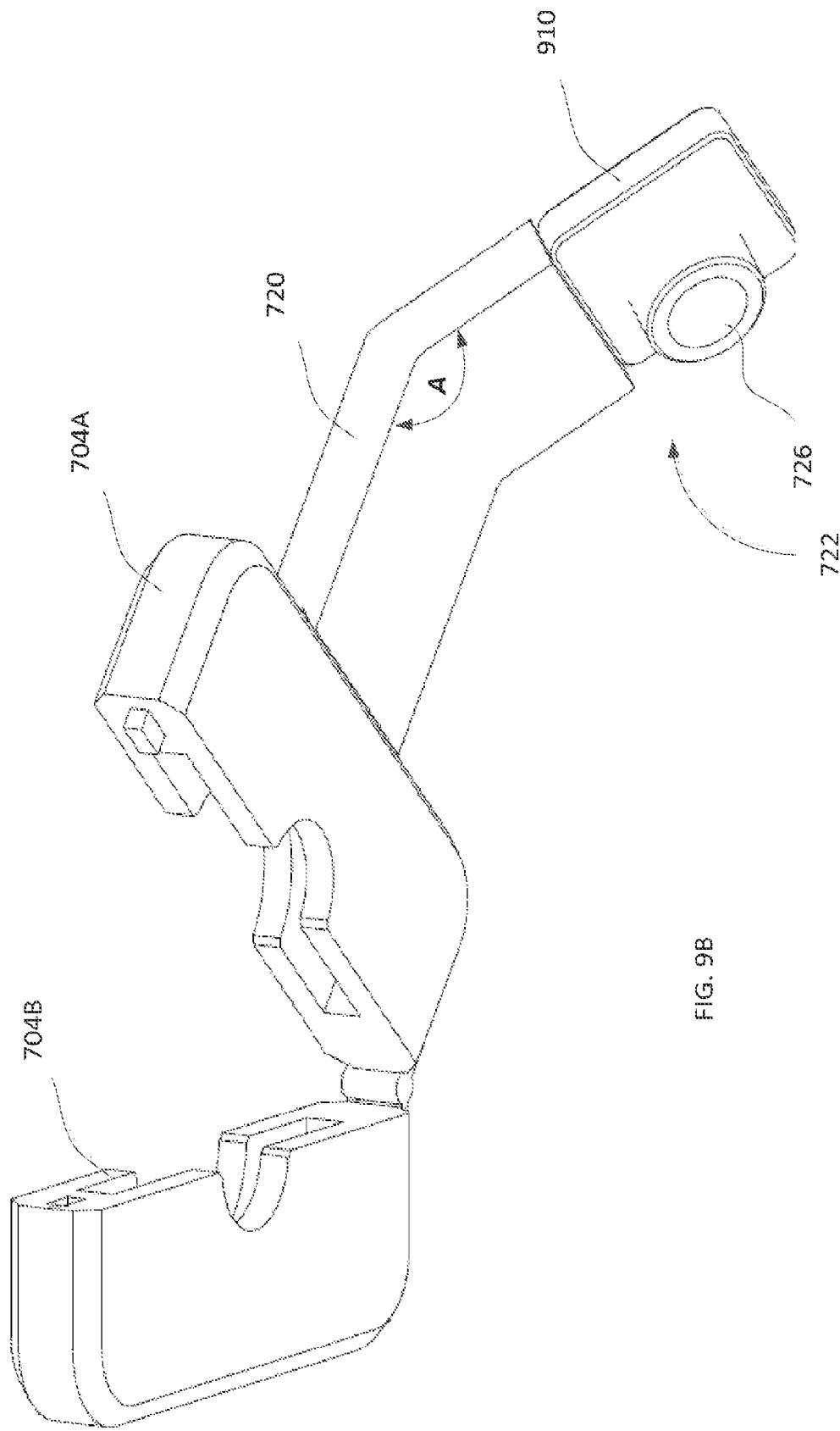

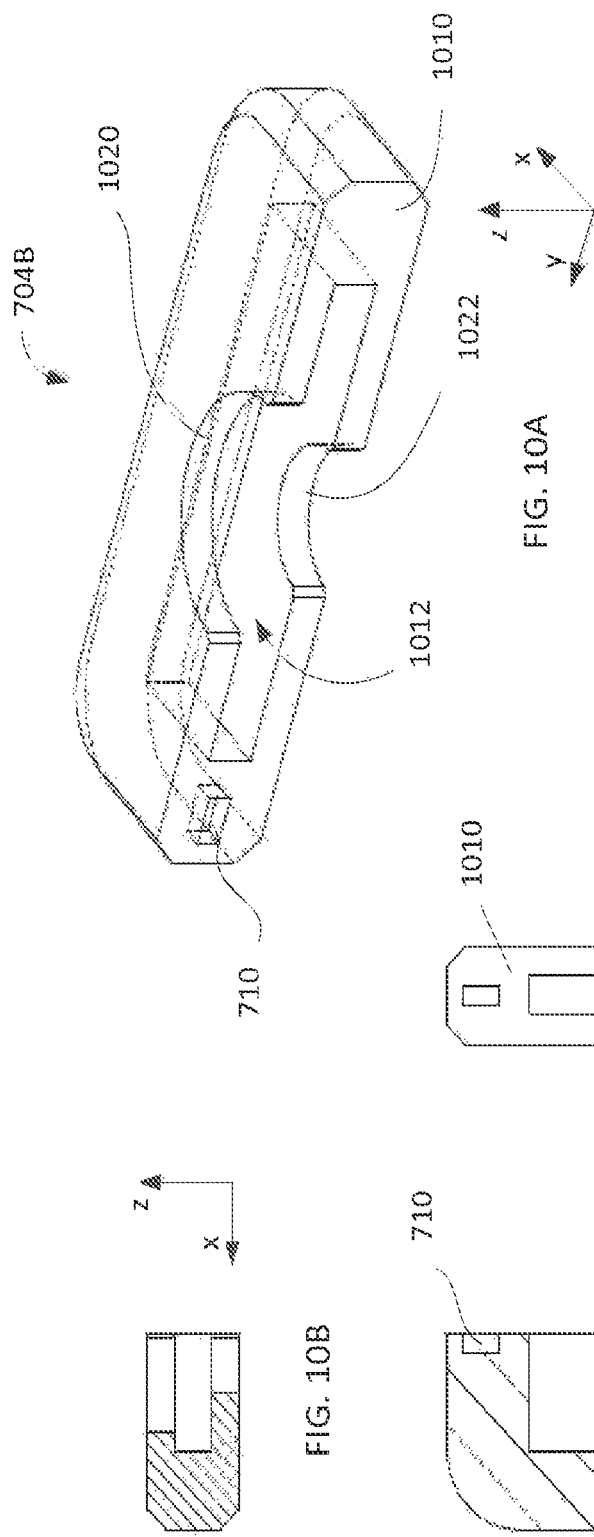

PERFORMING AND MONITORING DRUG DELIVERY

CROSS-REFERENCE TO RELATED APPLICATIONS

The present application claims priority from the U.S. Provisional Patent Applications No. 61/723,376 filed on Nov. 7, 2012 and titled "System and Method for Performing and Monitoring an Eye-Drop Procedure"; 61/806,471 filed on Mar. 29, 2013 and titled "System for Monitoring of Drug Management"; 61/808,425 filed on Apr. 4, 2013 and titled "System for Monitoring of Drug Management"; and 61/835,291 filed on Jun. 14, 2013 and titled "Eye-Drop Delivery Oversight Device". The disclosure of each of the above-identified patent applications is incorporated herein by reference in its entirety.

TECHNICAL FIELD

The present invention generally relates to application medical drops and injections and, in particular, to a device effectuating recording of the use of a medication-filled container, housed in the device, during the delivery of such medication to a tissue to determine regimen compliance and the amount of medication delivered to the tissue.

BACKGROUND

Patient's compliance with a prescribed therapeutic regimen can have a direct impact on the overall management of illness and clinical outcome, and, therefore, the improvements with regimen compliance will improve patient's health and reduce costs, both financial and physical associated with the therapeutic process. According to the data provided by the U.S. Department of Health and Human Services, diabetes affects over 25 million people in the US alone (National diabetes fact sheet: national estimates and general information on diabetes and prediabetes in the United States, 2011. Atlanta, Ga.: U.S. Department of Health and Human Services, Centers for Disease Control and Prevention, 2011), with, as estimated, 80 million people exhibiting signs of prediabetes. Though a strict adherence to diet, exercise, and drug regimens the diabetes sufferers can manage the symptoms associated with the disease indefinitely. Non-compliance to the insulin regimen is a significant problem for patients and health care professionals alike, and can exasperate the diabetes progression, with the unwanted results such as poor metabolic control, hospitalization for diabetes ketoacidosis, limb amputation, hyperosmolar coma, or even more detrimental consequences.

Because regimen compliance has been shown to be such a problem with patients and have such a significant impact on disease progression or presentation, many attempts have been made over the years to understand why patients have problems adhering to a regimen and how adherence can be improved. Furthermore, non-compliance to research study regimens significantly reduces the power and efficacy of clinical studies as an average compliance of 50% vs 100% requires an increase in sample size by fivefold to retain the sample study power. Thus having an accurate understanding of a patient's regimen compliance can help determine if a drug or therapeutic regimen is not working due to incorrect adherence or if an alternate regimen needs to be implemented by the physician. Unfortunately, understanding a patient's regimen compliance is difficult as patients often overestimate (incorrectly estimate) their adherence and multiple studies have found clinicians assessments of patient compliance to be unreliable.

Ideas for improving regimen compliance range from improving the doctor-patient relationship to improving patient oversight to improving patient health beliefs and providing education to patients regarding their disease. While each of these interventions has been studied, oversight is a major concern as over 95% of diabetic patients administering their own care, and regimen oversight has shown to significantly improve adherence. Accordingly, there remains a need for a system to document exactly how much medication delivered from a fluid filled container (for example, a syringe) actually gets into the delivery site (such as a patient's tissue), and according to which schedule such drug administration is carried out.

Eye-drop medications, both prescription and over-the-counter (OTC), are a mainstay of therapy for treating ocular complications. Eye drops are generally a preferred method of treatment because they are effective, substantially non-invasive, have limited systemic absorption and side effects compared to oral or intravenous medication administration, and in theory are easy to use. However, there is concern among ophthalmologists regarding the use of eye drops. Specifically, recent studies have found that compliance to eye-drop regimens is much lower than expected. This results in suboptimal therapeutic levels, which can reduce the efficacy of treatment. When eye drops are administered in a physician's clinic, trained technicians perform the procedure correctly; however, when eye drops are administered by patients (so called self-administration of treatment) they are not always administered correctly. The patient self-administering eye-drops does not always follow the procedural standards for drop administration and/or the proper timing for drop administration (for example for a twice a day regimen, the drops are not administered at 8 AM and 8 PM), which results in incorrect dosing. Even in cases where a clinician instructs a patient and/or asks a patient direct questions regarding an eye-drop regimen, or even when electronic monitoring of the procedure in employed, it is currently not possible to know if the drop intended for the eye actually got into the patient's eye or if they end up on the patients lid or if more than one drop was delivered into the eye. While some reasons for failed compliance are unavoidable, some of the causes (such as forgetfulness, confusion of similarly looking eye-drop containers or just plain error as to which eye drops to use, as well as failure to correctly follow an eye-drop administering procedure) are correctable.

Several devices have been developed to help patients adhere to eye-drop administering regimens. A system referred to as Travalert (manufactured by Alcon, Inc., Ft. Worth, Tex.), for example, utilizes electronic recording for unbiased, reliable measurements of instillation times and eye-drop counts. Other systems utilize timers and alarms to remind a patient that it is time to apply the eye drop(s) or weight measuring devices to ensure that medication has been removed from the bottle. Neither of these techniques for monitoring compliance with a procedure is meant to directly determine if and/or how much of the drop medication actually gets delivered to the patients eye(s). Instead, measurements performed by such systems are those of whether a patient attempts to administer the eye drops.

A study using video monitoring of eye-drop application has found that of subjects claiming not to miss an eye (when delivering eye-drops), nearly one third actually missed it and that out of all subjects using eye drops, approximately one third could not administer a drop onto the eye at all. Another study found that only about 9% of patients are able to correctly self-administer eye drops. Thus, even if patients are reminded about taking their eye drop medication and even if they have a scale for measuring dispensation of the eye drops, it is still not known if they drops ever make it into the eye or just land on the patients lids, cheek or other area outside the eye. It is also not known if the appropriate amount of medication finds its way into their eyes. Some patients waste copious amounts of eye drops trying to get the medication into their eyes and end up with too much or too little in their eye(s). Accordingly, there remains a need for a system to document exactly how much of a medication delivered from a fluid filled bottle, for example an eye-drop bottle, actually gets into the site it is to be delivered into, which for eye drops would be the patient's eye. There is also a need to a system that help patients understand how they are applying the drops, so that they can be educated on what changes need to be made to achieve the proper delivery of the drops/medication to their eye. Such a system should improve the management of ocular diseases, and should help to save health care costs by reducing the amount of drops wasted. In operation, for example, such a system provides an assessment of how much drug was delivered into the eye and provides an output based on which a better correlation can be defined of side effects (such as an irritation, for example, developed as a function of the volume of delivered drug) that a patient has from the drug to their application and application process. The system would allow for correlation of effects produced on an eye-lid as a function of a number of drops that get on the lid (instead of an eye) to better identify factors that lead to side effects and develop strategies for mitigation of such effects.

SUMMARY

Embodiments of the invention provide a method for monitoring patient-performed drug delivery from a hand-held container to a region of interest (ROI) associated with the patient's body. Such method comprises (i) applying hand input to a drug-delivery system to squeeze a drop of the drug from a tip of the container and to release said drop from said tip, where the drug-delivery system includes (a) the container containing the drug and (b) a container-holding system having a first (optionally—size-adjustable) frame component structured to house (optionally—removably) the container therein along an axis thereof and a second frame component extending transversely with respect to the first frame component, the second frame component carrying an imaging camera having an optical field-of-view (FOV), an optical detector, and enabled to record images of a scene within the FOV; such that the FOV covers the tip, the ROI, and a space separating the tip from the ROI. The method further comprises (ii) recording a series of image frames, each frame representing a corresponding position of the drop in said space; and (iii) producing an identifier representing whether said drop landed in the ROI. Such identifier may be produced or formed as a conclusion based on an observation of the series of image frames. Alternatively or in addition, such identifier may be generated—for example, in an automatic fashion—based at least on a correlation figure of merit calculated in reference to an image frame and a template containing an image of the tip. The hand-held container may include a squeezable bottle and the ROI may include includes a patient's eye. The producing an identifier may include identifying a position of the tip that is common for all image frames from the series. The step of generating may include determining target image frames from the series, where target image frames represent only an advancement of said drop through said space. In a specific implementation, the producing an identifier includes generating an identifier representing whether said drop landed in the ROI based at least on a correlation figure of merit calculated according to $$\mathrm{Cor}(x, y) = \frac{\sum_i \sum_j [T(i, j) - \overline{T}][F(i+x, j+y) - \overline{F}(x, y)]}{\left\{\sum_i \sum_j [T(i, j) - \overline{T}]^2 \cdot \sum_i \sum_j [F(i+x, j+y) - \overline{F}(x, y)]^2\right\}^{1/2}},$$

wherein $T(i, j)$ is an irradiance value corresponding to a pixel of the template, $F(i, j)$ is a pixel irradiance value of the image frame, $\overline{T}$ is an average of pixel irradiance values calculated over the template, and $\overline{F}(x, y)$ is a average of the pixel irradiance values of a local image area of the image frame.

The method may optionally include identifying a closed boundary of the ROI in a target image frame based on color segmentation of an image contained in said target image frame and, in addition or alternatively, determining a position of the drop relative to the ROI based at least on the FOV and a size of a pixel of the optical detector. The step of applying may include applying a hand input to a drug-delivery system to squeeze a drop of the drug from the tip of the container and to release said drop from said tip, wherein the second frame component includes a light source (whether visible or infrared) facing the scene, while the method may additionally contain a step of illuminating said drop with said light source for the recording of each image frame. In a specific embodiment, the recording a series of image frames can be effectuated in IR portion of the spectrum and in absence of a light source at the second frame component.

Embodiments of the invention also provide an article of manufacture that includes a mount dimensioned to (optionally removably) secure a chosen hand-held container having a tip, the mount having first and second frame components, the first frame component including first and second ends and length (that is optionally telescopically adjustable) along the fluid container, the second frame component connected to the first frame component at an angle, the second frame component carrying (i) a lens with a field-of-view (FOV) that covers a vicinity of the tip once the fluid container is secured in the mount and (ii) an optical detector. The optical detector is operable to detect visible light and/or IR light. Such mount further includes a source of light (visible and/or IR) disposed on the second frame component such as to illuminate an area in the vicinity; and electronic data-processing circuitry in operable communication with said optical detector and programmed to record and process the received optical data to determine temporal and spatial characteristics of the illuminated area. The optical detector is disposed in spatial coordination with the source of light to receive, from the lens, an irradiance distribution corresponding to light reflected by the area illuminated with the source of light. The angle may be adjustable, with a hinge operably connecting the first and second frame components, between about 0 degrees and 270 degrees. In a related embodiment, the angle may be fixed.

The mount may further include a ring-like adapter structured to ensure that the fluid container is removably secured in a portion associated with a neck of said fluid container; the adapter may be adjustable to accommodate fluid containers of variable sizes. An embodiment may additionally include a video-recording means in operable communication with the optical detector.

In a specific case, when the hand-held container includes a squeezable bottle filed with a drug to be delivered to a patient's eye and the bottle, in operation, is squeezed by the patient to form a drop of the drug at the tip and to effectuate such a delivery, (i) the area in the vicinity includes the tip, the patient's eye, and a space separating said tip and said eye, and (ii) the article additionally includes a tangible, non-transitory storage medium with program code stored thereon. Such code, when executed by the electronic data-processing circuitry, causes said circuitry to record a series of image frames, each frame representing a corresponding position of said drop in said space; and generate an identifier of said spatial and temporal characteristics based at least on a correlation figure of merit calculated in reference to an image frame and a template containing an image of the tip. The spatial and temporal characteristics of the area illuminated with the light source represent one or more of (i) a merit of success of delivery of the drug to the patient's eye, (ii) a first value associated with an amount of drug dispensed from the hand-held container, (iii) a second value representing time of drug delivery; and (iv) a third value representing a proportion of the first value delivered to the patient's eye. In one embodiment, the article may be further equipped with an infra-red heat detection optical system which can increase the differentiation between the medication and the tissue on imaging thus improving the ability to system to detect the eye drop and follow its path in some patients when compared to a visible light system.

In one embodiment, the images are then analyzed by image analysis software which will be able to partially or fully automatically detect when the drug administration occurred, whether or not a drug administration was applied correctly and exactly where and how much of the medication was dispensed. This software can be located on computer equipment that is separate from the image acquisition and image storage devices. The software can also be packaged in a processor in the proximity or as part of the image acquisition and storage devices, so as to give the patient prompt feedback on the success of the drop delivery. In one embodiment of the article, the regimen compliance analysis may be done by individuals in a secured reading center, which may compile data recorded by the article.

In one embodiment, the article may be powered by an internal battery. In another embodiment, the article may be powered via a corded connection with an external power source.

In one embodiment, the article may transfer captured images wirelessly or via a wired connection.

BRIEF DESCRIPTION OF THE DRAWINGS

The invention is more fully understood by referring to the following Detailed Description in conjunction with the generally not-to-scale Drawings, of which:

FIG. 4A illustrates the exploded view of the embodiment, while FIG. 5B shows an external device operably wired to the embodiment.

FIGS. 9A, 9B are diagrams showing the alternative embodiment of FIGS. 7 and 8;

FIGS. 10A, 10B, 10C, 10D illustrate schematically various components of the embodiment of FIGS. 7 and 8;

DETAILED DESCRIPTION

Figure 1A:
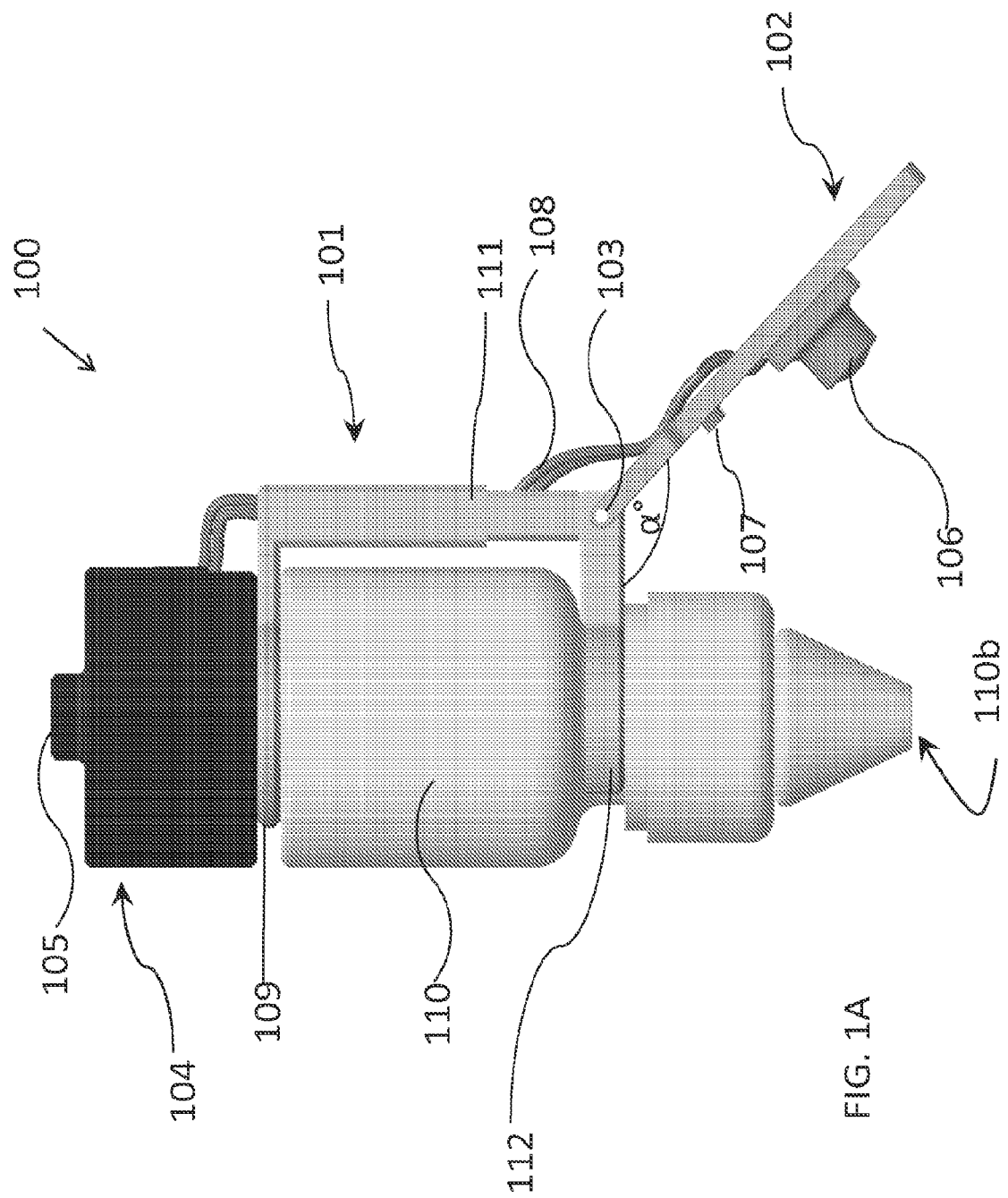
FIGS. 1A, 1B, 2, 3, 5A, provide illustrations to an embodiment of the invention in which the frame elements are repositionably attached to one another via a hinge.
Figure 1B:
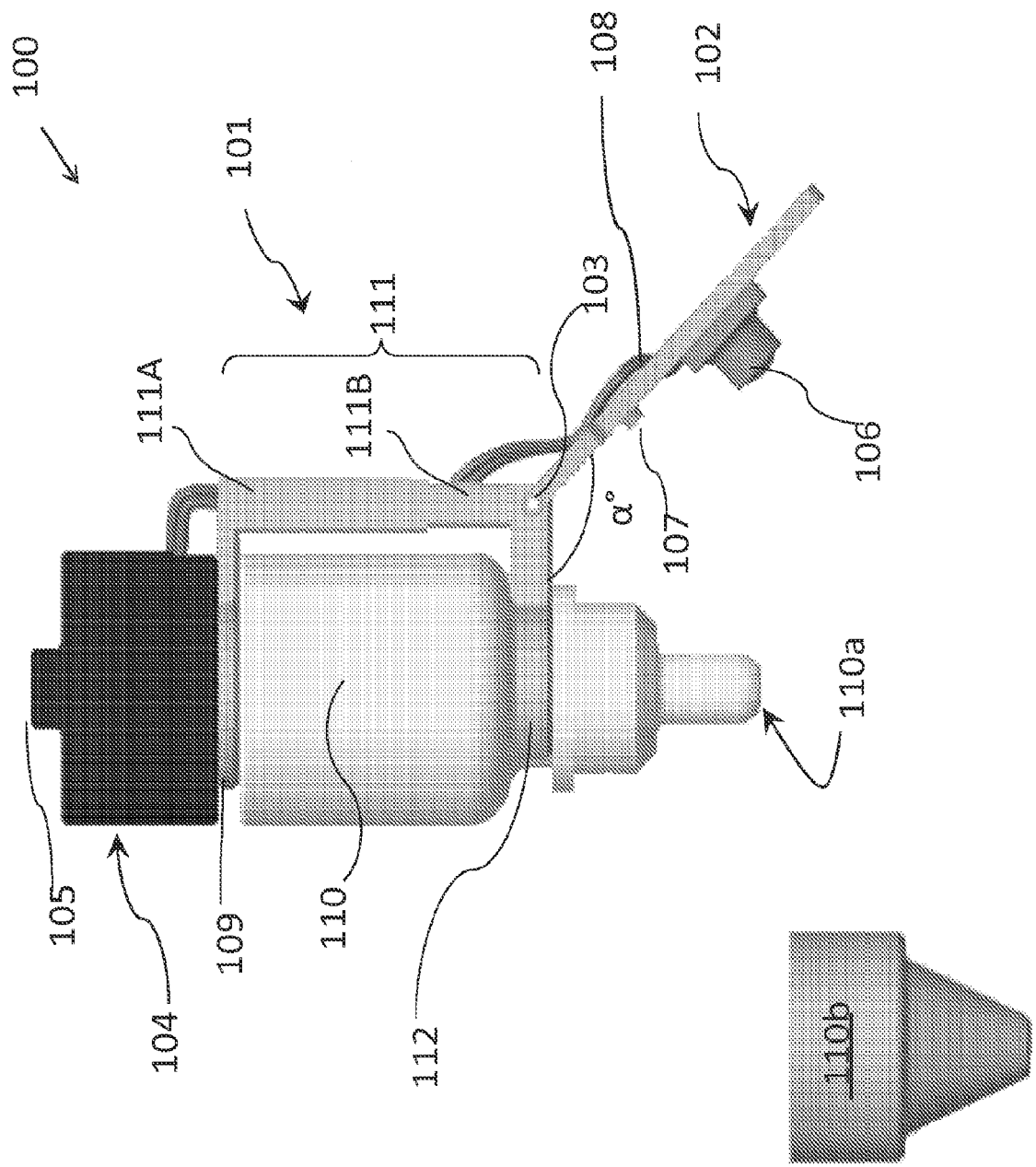
Figure 2:
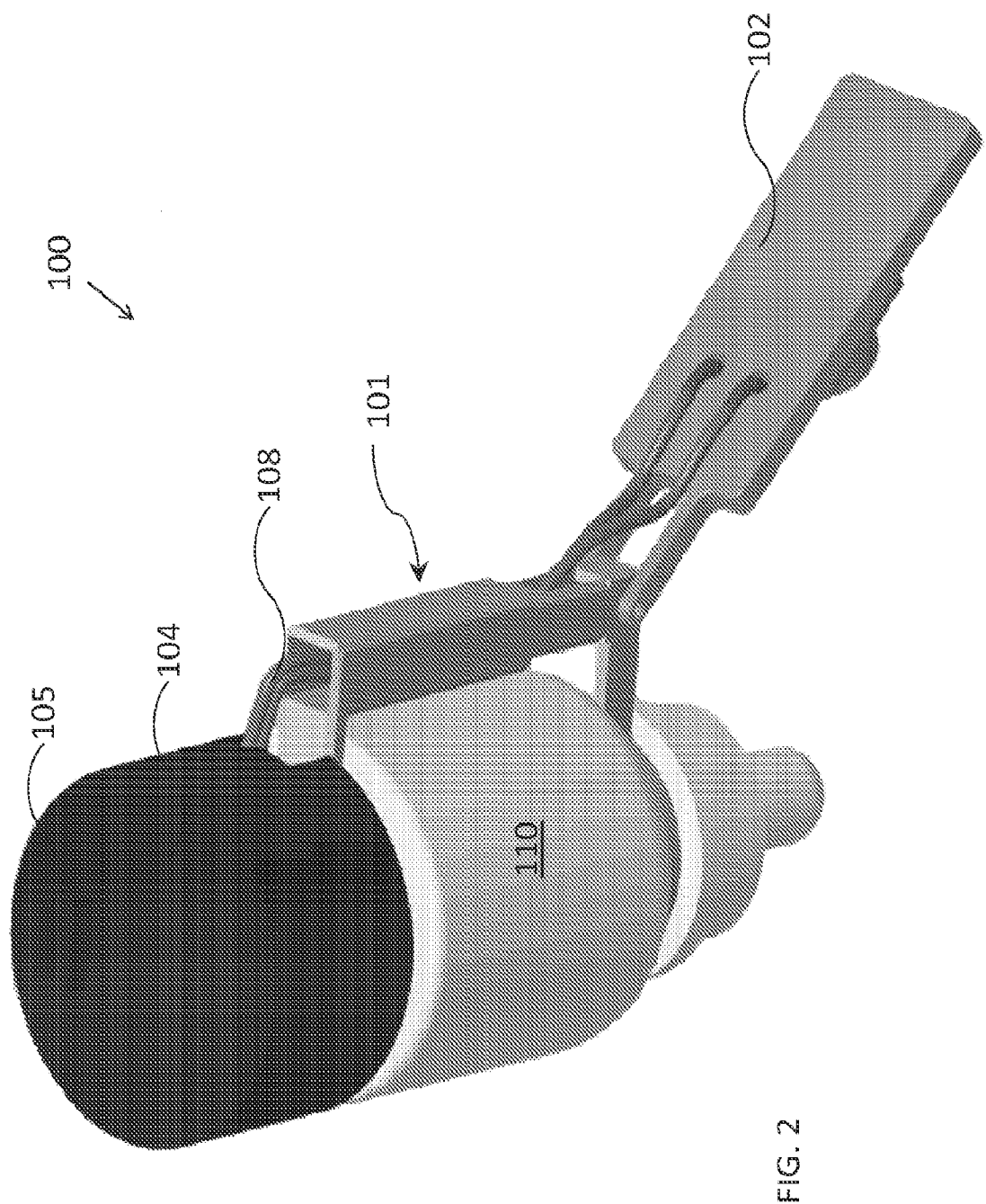

Embodiments of the present invention provide a medication adherence intervention device for chronic health conditions such as Glaucoma and Diabetes. This device is structured to enable physicians to have a direct and impartial understanding of a patient's drug regimen adherence so as to allow for discrete intervention to improve drug delivery and/or compliance so as to prevent disease progression. Each instance of drug application is recorded by a portable imaging device. The images can then be reviewed by the patient, their physician, a reading center, and/or imaging software. A report can then be generated, allowing the patient and/or his physician, physician's staff or such other health care entities or people that might participate or assist in the patients care to intervene when necessary to improve therapeutic regimen delivery to the tissue or eye and/or compliance and thus improve patient health and disease management. One embodiment of the device has been designed to fit standard insulin syringes without interfering with the injection procedure to monitor diabetes management or to fit a standard eye drop bottle for monitoring of glaucoma drug administration. As such, the device is superior to current monitoring methods such as MEMS caps, pharmacy refill records, and pill counts as it will allow for direct visualization of drug administration rather than rely on indirect monitoring methods which may not be indicative of actual regimen compliance.

Embodiments of the present invention address the need for knowing if a medication delivered in a fluid filled syringe or drop bottle actually arrives to the site it is intended to be delivered to, and gives the potential to automate the drug delivery assessment. According to the idea of the invention, and instead of relying on indirect compliance measurements (for example, weighing drug container and/or timers/alarms), an embodiment of a system of the invention employs a video-monitoring means in juxtaposition with the fluid-filled container to record the actual administration of fluid to the tissue, which can be reviewed and quantified. In addition, the recorded images can be time-stamped to provide a record of the exact time of administration. The data acquired and, optionally, recorded by a device of the invention can be further transferred and/or stored on a tangible computer-readable medium, for example, for visual display and/or visual and digital assessment of compliance with the procedure. Such data can then be transferred to a remote server or reading center, where it can be reviewed manually or automatically, and a written report detailing actual drug delivery to the tissue as well as the timing of the delivery can be provided to the physician and/or patient. Additionally, these data can be further analyzed and a summary report can be provided which includes average and/or median variance(s) from a prescribed dosing time, as well average and/or median variances in the amount of the drug delivered to the tissue as well. Statistical data, such as standard deviation and such other statistical analysis as may be found useful can also be provided. All of this assessment may be done by the reading center and/or by the image analysis software included in the device.

In reference to the drawings, FIGS. 1A, 1B, 2, 3, 4A, 4B, 5A, 5B provide diagrams illustrating schematically different views of the components of a monitoring system for eye drop administration as well as the monitoring system in the assembled form. The embodiments 100, 500 are referred to as Eye-Drop Application Monitor (EDAM) and are shown in cooperation with a container 110 filled with eye drops and having a nozzle 110a that is covered, when not in operation, with a cap 110b. The embodiment 100 includes a first frame element or arm 101 configured, as discussed below, to accommodate the container 110, and a second frame element 102 affixed to the first frame element 101. In one implementation 100, the second frame element 102 is adjustably and/or repositionably connected to the first component 101 with a hinge 103. The second frame component 102 is generally disposed at an angle α with respect to the first frame component 101. This angle α can range from about 60 to about 200 degrees, preferably from about 90 to about 170, and even more preferably from about 120 to about 150 degrees. In a specific implementation, the angle α is about 135° to facilitate an optimal viewing of the eye drop procedure by a camera of the embodiment, as detailed below. (Alternatively, the second frame element 102 may be fixedly connected to the first frame element 101 at an angle β, as shown in FIG. 4A, 4B, with β being within a range from about 60 to about 200 degrees, preferably from about 90 to about 170, and even more preferably from about 120 to about 150 degrees. In a specific implementation, the angle β is about 135° to facilitate an optimal viewing of the eye drop procedure by a camera of the embodiment, as detailed below.) The position of the video camera and lens are generally such that the tip of the drop bottle is within the field of view of the video image, more preferably no more than 50% into the image, and most preferably extending around 25% into the video frame.

In further reference to FIGS. 1A, 1B, 2, 3, 4A, 4B, 5A, 5B, the first frame element 101 includes a portion 111 with the first and second ends that are configured as the foot portion 109 and a clasp 112. The first frame element 101 optionally has an adjustable length that can be changes from inside the portion 111 (for example, telescopically, and optionally under a load such as a spring load, by repositioning one sub-portion 111A of the portion 111 inside another sub-portion 111B) to allow for insertion of a fluid containing bottle of different lengths or heights. The foot portion 109 is shaped to provide contact, on one side of the base portion 109, with a bottom of the fluid-filled container 110 such as to spatially stabilize (optionally—tensionably under the load of the spring within the telescopic portion 111) the container in the first frame element 101 between the foot 109 and the clasp 112. As shown in FIG. 4B, one of the sub-portions 111A, 111B can be optionally equipped with a mounting arm brace 430 dimensioned to support the sub-portion 111A when the portion 111 of the first frame element 101A is in a fully contracted state.

Figure 5:
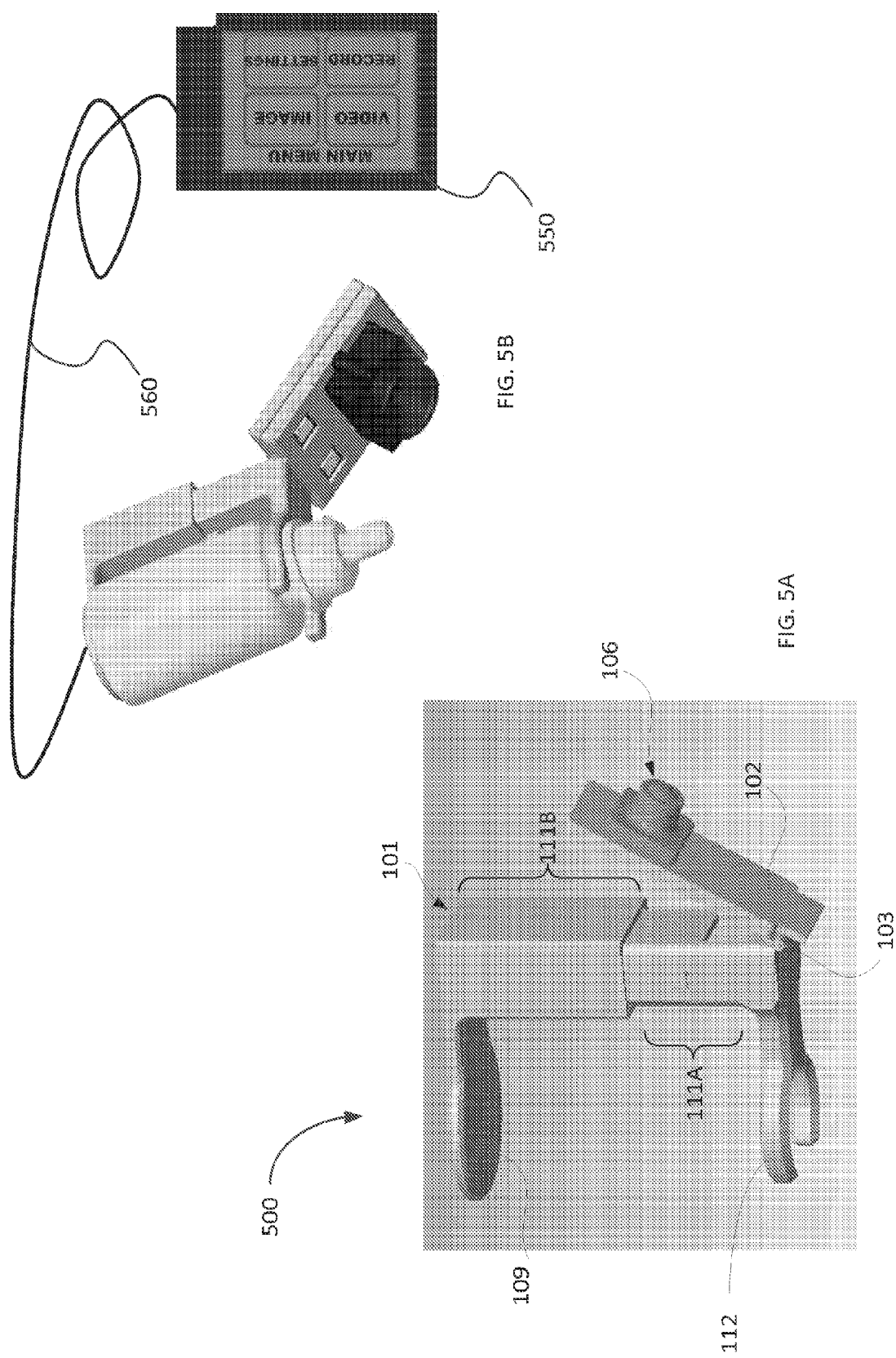
Figure 6:
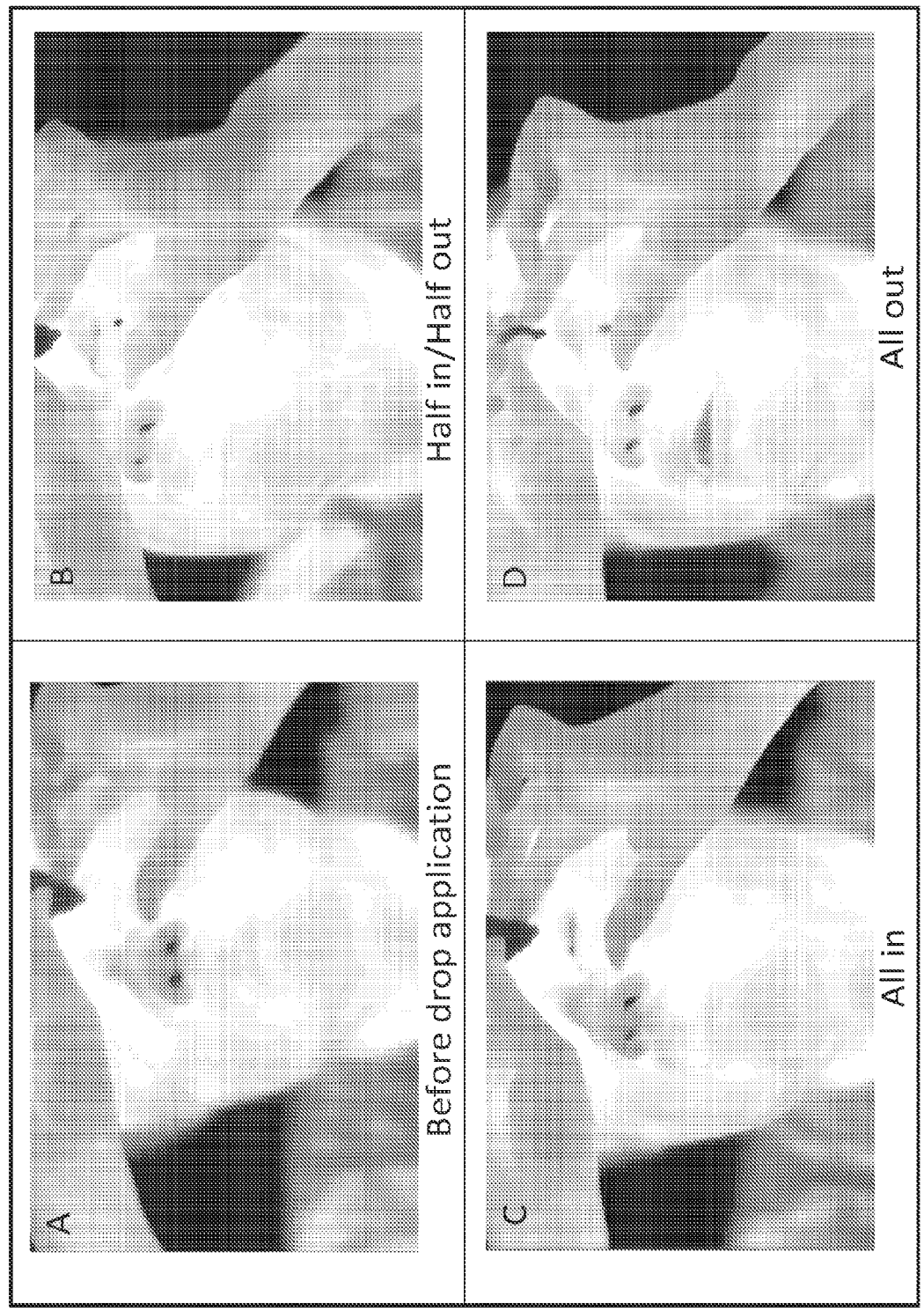
FIGS. 6A, 6B, 6C, 6D are images representing video-frames acquired with an embodiment of the invention during the eye-drop delivery procedure.

The embodiment of the device may be additionally optionally equipped with a base unit 104, configured as a holder for a power unit (such as an optionally replaceable and/or rechargeable battery) and/or auxiliary hardware (such as electronic circuitry and/or programmable processor and/or tangible storage medium) required for operation of the embodiment 100. In a related embodiment, however (such as that of 500, FIG. 5), the base unit 104 may be absent at least one of the power unit and the auxiliary hardware elements may be disposed within or in juxtaposition with the frame element or arm 101. Optionally, the base unit 104 is equipped with a port 105 adapted for operable connection with a computer or another external electronic device (not shown) in a fashion similar to that of an USB port, for example, or an electrical plug. The port 105 is judiciously configured for transfer of data and/or power between an external device and the base unit 104 (for example, to recharge a battery within the base unit 104 or to transfer the data collected by the system 100 to the external electronic device). In a related implementation, the port 105 is adapted to facilitate spatial docking of the system 100 at an external electronic platform (not shown). Such docking platform can allow for charging and data transfer, weighting or such other functions as are found to be beneficial. In an embodiment optionally devoid of base unit 104, the operable, data- and energy-transfer enabled connection between the camera 106 and the external battery and/or data storage medium and/or data-processing circuitry 550 may be configured either through a direct wire-based connection 560 or wirelessly (with the use of Bluetooth, intranet, or internet based communication means), as shown in FIG. 5B. This would allow for the battery and image/video recording software to be housed in a separate unit that could be placed on a table or in one's lap during use of the device.

Figure 3:
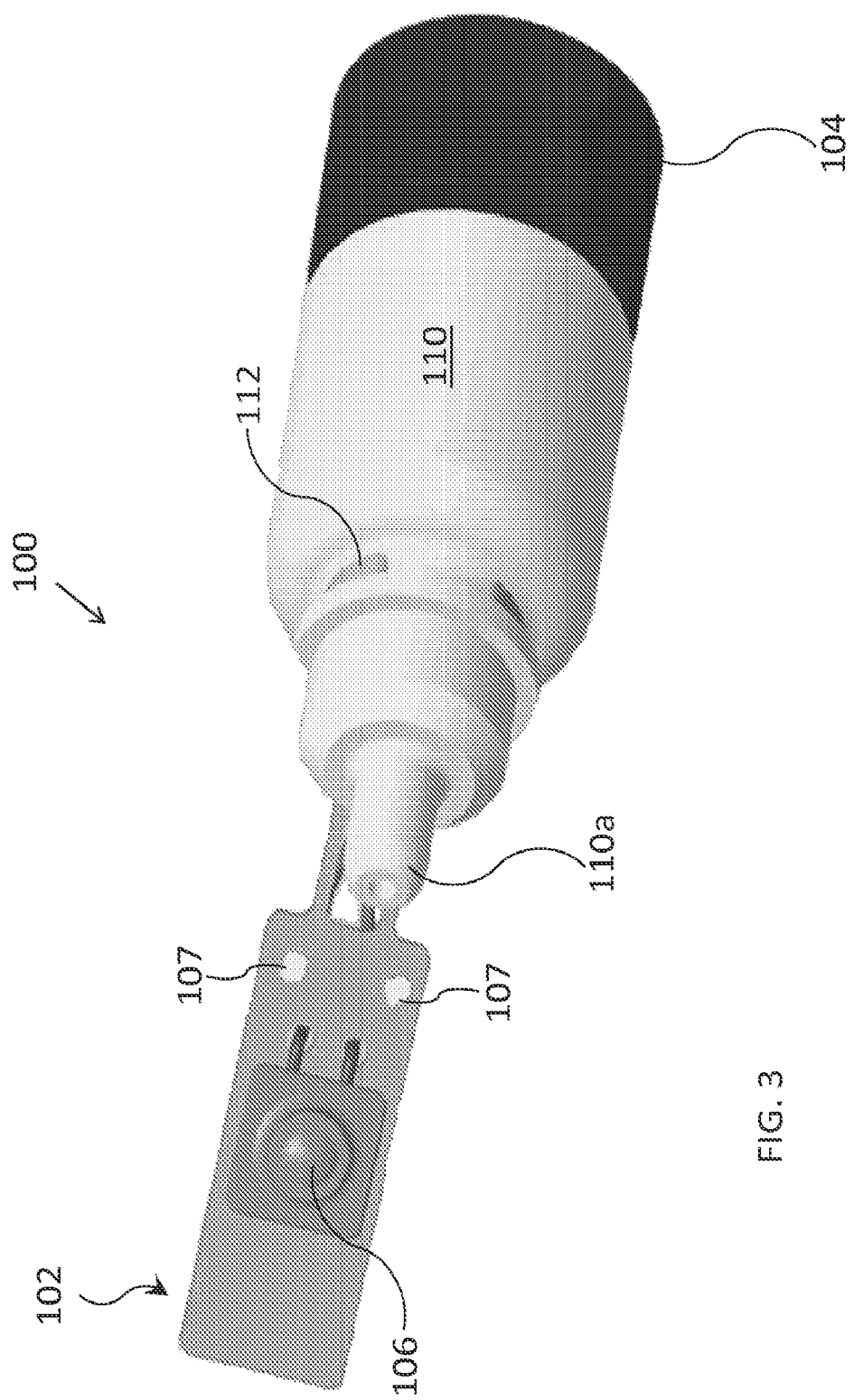
Figure 4:
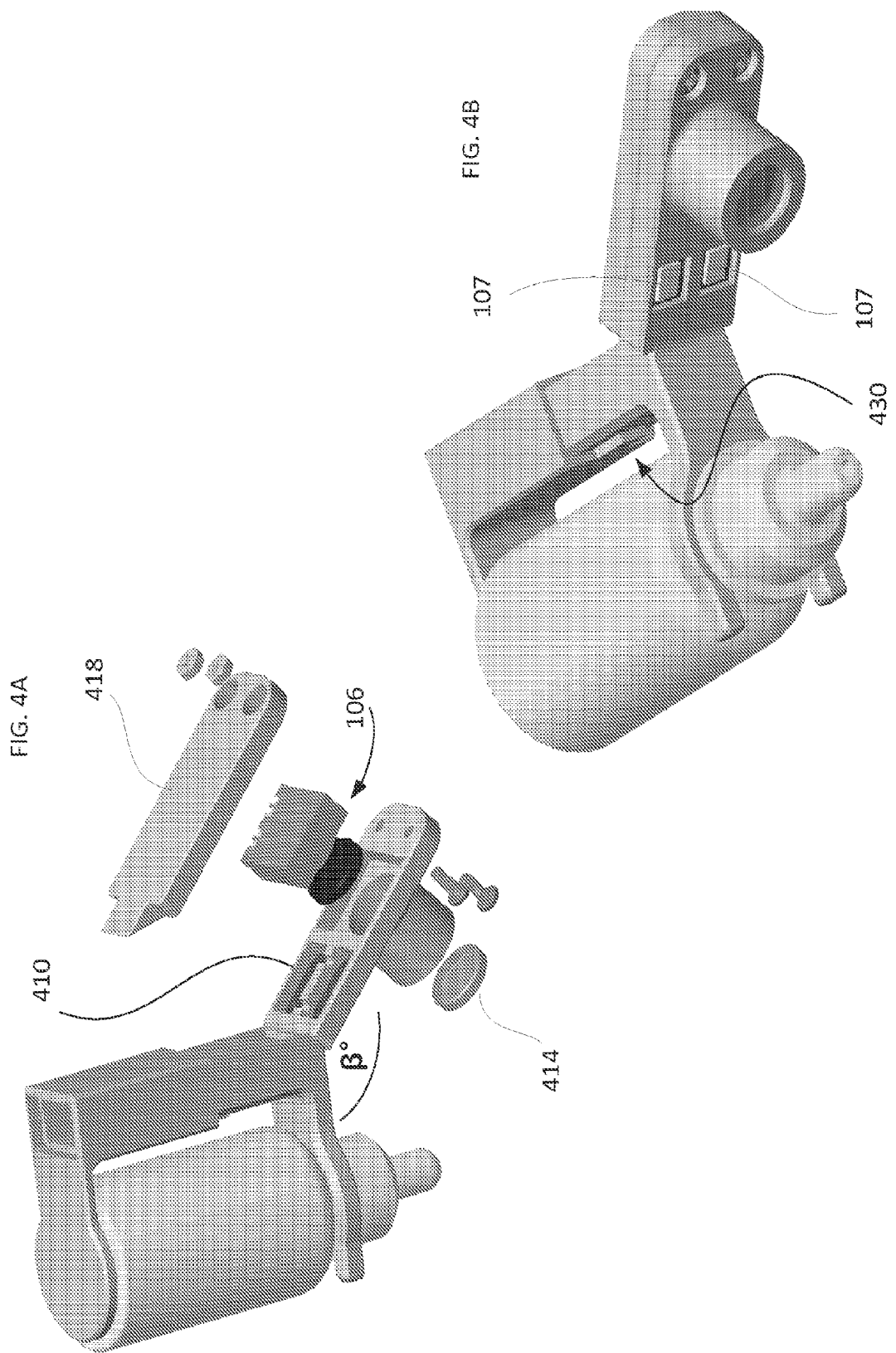
FIGS. 4A, 4B, 5B illustrate an embodiment of the invention in which the frame elements are affixed to one another in a permanent spatial configuration.

In further reference to FIGS. 1A, 1B, 2, 3, 4A, 4B, 5A, 5B the second frame component 102 (shown as a handle, optionally movable angularly about the hinge 103) carries, on its surface that faces the clasp 112, a camera 106 that is optionally equipped with a micro-optical system including a lens. The frame component 102 additionally carries at least one light source 107, the light from which provides required illumination of a scene an image of which the camera 106 is enabled to capture. The affixation of the camera 106 at the frame component 102 can be established with the use of an appropriate adhesive or an alternative mounting means know in the art (such as with the use of a threaded indentation or bore formed in the body of the component 102). The light source(s) 107 may include an LED, a halogen bulb, or another source of light having appropriate dimensions. The light source(s) 107 may use light in the visible light 380 nm-700 nm) and the typical illumination intensity is approximately 250 millicandelas (mcd), though this can vary, depending on the wattage used for powering the light source(s). In all cases, it needs to be below levels which could cause light induced retinal toxicity. Based on current technology, the visible light illuminating light source(s) 107 require approximately 120 mW of power, provided by the electronic circuitry 410. FIG. 3 illustrates cases in which the embodiments of the device include two light sources 107. When several light sources 107 are disposed at the second frame component 102, such light sources 107 may be spatially distributed around the camera 106 in a pre-determined geometric fashion (for instance, circular, or polygonal depending on the number of the light sources 107). The spatial positioning and/or orientation of the camera 106 and the light source(s) 107 is such that, in operation, when the eye-drop container is secured between the clasp 112 and the foot 109, the illumination of the eye-drops emitted from a nozzle 110a by the light source(s) 107 is sufficient to acquire informative images of the eye-drops from the time they leave the eye drop tip until they enter the eye or miss the eye. In one embodiment, the tip of the eye drop bottle is seen at the edge of the image, so that its direction can be recorded from the time it leaves the bottle until the time it contacts the tissue. Elements 414, 418 annotate structural components used to support and house the camera unit 106.

The camera 106 and/or the light source(s) 107 are electrically connected with the base unit 104 via an electrically-conductive member 108. In one embodiment, such member 108 includes an electrical wire or bus passing through the hollow or the internal space in the slidably-adjustable portion 111. In another embodiment (not shown) the electrically-conductive member 108 may be disposed outside of and substantially adjacent to the portion 111 or even embedded within the body/walls of the portion 111.

An optional lens of the camera 106 preferably has a field of view of about 60 degrees to about 180 degrees (defined by a full linear angle). In one embodiment, for example, a wide angle lens with about 120 to about 180 degree field of view can be used, or, preferably, with the field of view from about 150 degrees to about 180 degrees. While any lens suitable for imaging at a distance of about 5 mm to about 50 mm between the eye and the lens are acceptable, generally a wide angle lens are preferred. In a related embodiment, the working distance between the camera 106 and the eye ranges, in operation, between about 5 mm to about 100 mm, more preferably between 10 mm and 50 mm, and most preferably 15 mm and 35 mm. Accordingly, the optional lens of the camera 106 has a focal length from about 0.2 mm to 4 mm, or more preferably from about 0.5 mm to about 2.54 mm, and most preferably from about 0.75 mm to about 1.5 mm. In practice, a lens' F-number may range from about 1 to about 5, or more preferably from about 1.5 to about 3. An image detector associated with the camera 106 (not shown, for example behind the camera 106 in the component 102) is configured for acquisition of optical data representing the scene including the vicinity of the nozzle 110a (such as, for example, eye drops emitted by the nozzle 110a and an eye of a patient to which these eye drops are directed). In general, a CMOS based detector with size ranging within the range of about ⅕"-½" and pixel count in a range of 400*400 to 2048*2048 or higher as better detectors become available, preferably ⅓", with a pixel count of about 1024*1024 or greater is used. Additionally, an embodiment of the monitoring system may contain a user-interface with a time-counting and/or sound- or light-emitting mechanism and/or wireless transmitter transmitting data to an external patient-readable to remind the patient that it is time for their next eye drop to be administered. The action of turning on the embodiment and administering another drop or depressing a relevant trigger of the user interface could then stop or re-set such notification reminder (which may be configured as light alert, email or text to the patient's phone, or sound alert, for example, to name just a few).

While the current design allows for use with multiple different sized fluid filled containers, it being understood other designs in which the unit is fixed to fit a single fluid filled container, and has some or no moving parts, may also be utilized. It being understood that fluid filled containers include eye drops, ear drops, nose drops, oral drops, dermal drops, syringes (as further discussed below), and any other such fluid filled containers as can be envisioned or used for delivery of medications in humans, and or animals. In the case where the drops are delivered from a fluid filled tube that is inserted into a fluid filled container, the camera can be affixed to the fluid filled tube.

The following examples of experimental studies illustrate the use of the eye-drop application video-monitoring device (such as that used in the embodiments 100 of FIGS. 1A, 1B, 2, 3, 4A, 4B, 5B and 500 of FIG. 5A) in assessment of a patient's eye-drop medication regimen. This is particularly important for clinical studies of new medications being delivered by in the form of an eye drop, to allow the researcher to determine if a patient's failure to respond to a drop regiment is because the medication did not work or if it was because the patient did not take the medication at the prescribed time, or it did not get into their eye. If side effects occur, an embodiment of the invention also facilitates a determination of whether such effects resulted from overuse of the drops, or other problems with delivery which might not have happened if they had been delivered correctly. Finally, for eye-doctors treating patients for conditions such as glaucoma, it is important to know if the reason for a patient's lack of response is a failure of the medication to work, or due to incorrect dosing or such dosing in which a required number of eye-drop is not delivered into an eye, as such knowledge will affect the manner in which the doctors determines future therapy regimen(s). In the event of side effects, it will be possible to determine if they are a result of improper delivery, excess delivery or simply the medication itself. From this information a more accurate adjustment can be made to the patient's medication regimen. The required adjustment may be as simple as retraining the patient as to proper delivery of the drops to the eye, or a selection of another medication. In the event when the failure to achieve proper delivery of the drug is caused by arthritis, a tremor, inability to properly train, or other ailments alternative glaucoma therapies such as laser surgery (such as Selective Laser Trabeculoplasty (SLT), Argon Laser Trabeculoplasty (ALT), Micropulse Laser Trabeculoplasty (MLT), and Laser Cyclophotocoagulation)), incisional surgery (Trabeculectomy, Valve, Canalostomy, Seton surgeries) oral agents or some combination thereof may be prescribed and/or performed.

Accordingly, in one experiment, ten eye drops per subject, placed in the container 110 of the embodiment 100, were dispensed in an eye, outside of the eye, and at the transitional region corresponding to at the edge of a lid and/or corner of the eye, multiple times. Video-recording was taken of the dispensing procedure, in addition to which an independent skilled eye-care provider/observer also documented a number of drops that, according to his observation, were delivered to the eye in comparison with a number of the eye drops that missed the eye. Processing of the video-recording with data-processing circuitry (such as a computer processor) established that in 100% of the video-images it was possible to determine with certainty whether a given drop was delivered into the eye. The comparison of the results with the individual observation is presented in Table 1. There exists variability in the actual results between what is recorded by video and what the skilled eye care provider observed. Due to the speed and/or rate with which the drop(s) enter the eye, the capacity of the eye to absorb the volume of delivered medication is often exceeded and, as a result, accuracy of visual determination of compliant delivery of the drop(s) to the eye by a patient or an observer is compromised. This is particularly true for drops that are used for dry eye or are non-preserved and do not cause pain and irritation when they are instilled, as it is harder to tell if they got into the eye. However, with the video record it is possible to tell with 100% certainty if the drop got into the eye.

TABLE 1

| Experiment | Video | | | | HumanObserver | | | |
|---|---|---|---|---|---|---|---|---|
| # | In | Out | 50/50 | Unsure | In | Out | 50/50 | Unsure |
| #1 | 2 | 3 | 0 | 0 | 2 | 2 | 0 | 1 |
| #2 | 2 | 3 | 0 | 0 | 2 | 2 | 0 | 1 |
| #3 | 3 | 2 | 0 | 0 | 3 | 1 | 0 | 1 |
| #4 | 3 | 2 | 0 | 0 | 3 | 2 | 0 | 0 |
| #5 | 2 | 2 | 1 | 0 | 3 | 2 | 0 | 0 |

Example 2

An infrared incarnation of the camera (such as the camera 106 of the embodiment 100 and, in this specific experiment—the Atom 1024IR camera), was used to assess the quality of imaging and recordation of the eye-drop delivery to the target (the eye) With the use of such recording means it was possible to clearly see the drop which appeared black against the white back-drop of the skin of the patient. Here, in reference to FIGS. 6A, 6B, 6C, and 6D, the embodiment of the invention had a capability to detect temperature differences of less than 50 milliKelvin (mK), with the pixel a resolution of 1024×768 (17 micron pixels), a 30 Hz XGA or 60 Hz VGA frame rate, and a thermal time constant of less than 10 ms. The experiment was carried out in an air conditioned building at 78 degrees F., while the eye-drops were at a room temperature. A temperature flush could also be observed when a drop entered the eye, which returns to a normal temperature and restores its IR signature in seconds afterwards. In an alternative version of the experiment, eye-drops were refrigerated and similar eye-drop delivery into an eye and associated recording/monitoring produced similar results.

In addition or alternatively to the use of the monitoring-device structure discussed above in reference to FIGS. 1 through 6, the idea of the invention may be used to visualize the injection of insulin or some other drug.

Figure 7:
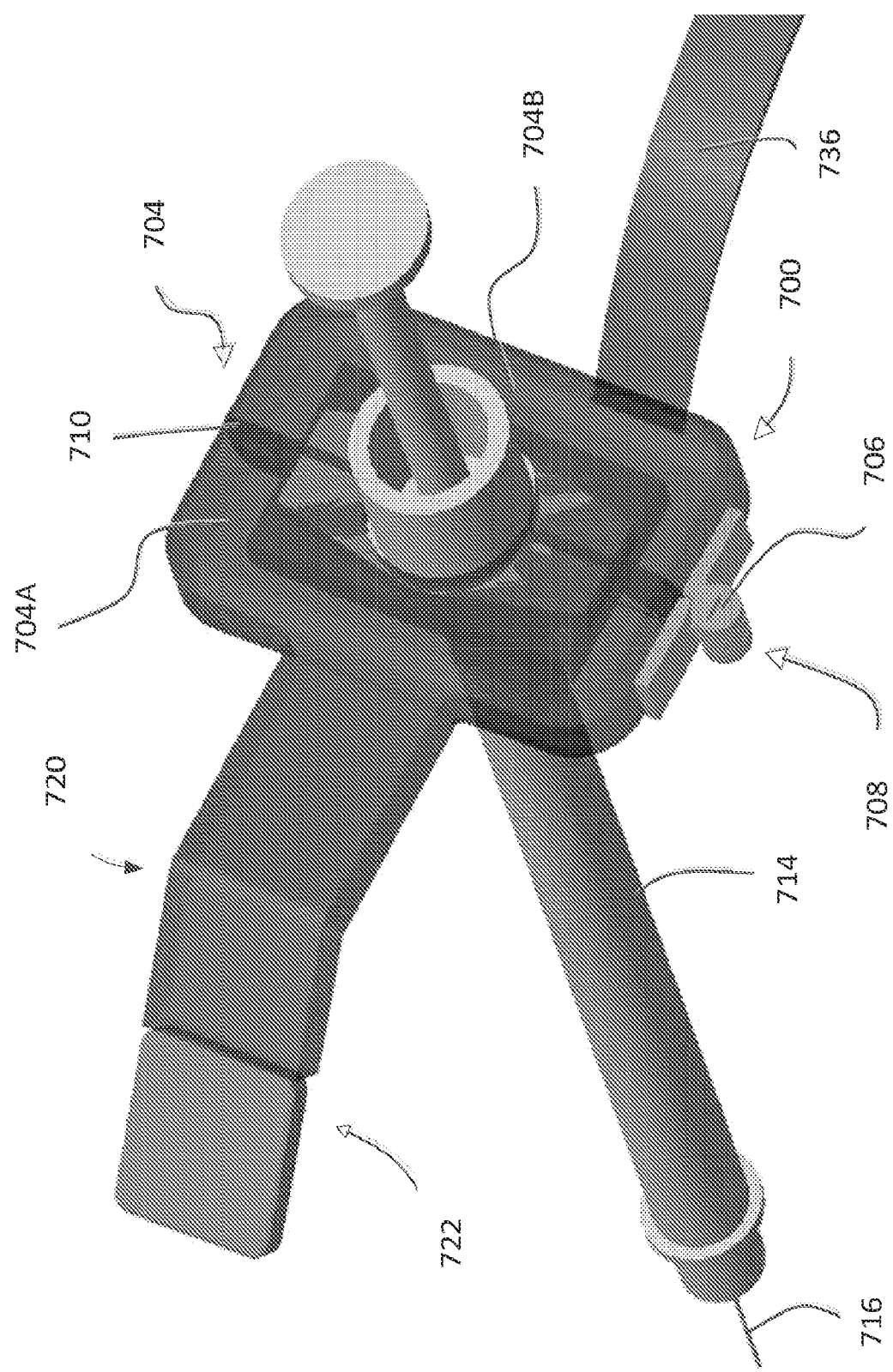
FIGS. 7 and 8 are diagram showing the use of an alternative embodiment of the invention, that contains and supports an injection unit.
Figure 8:
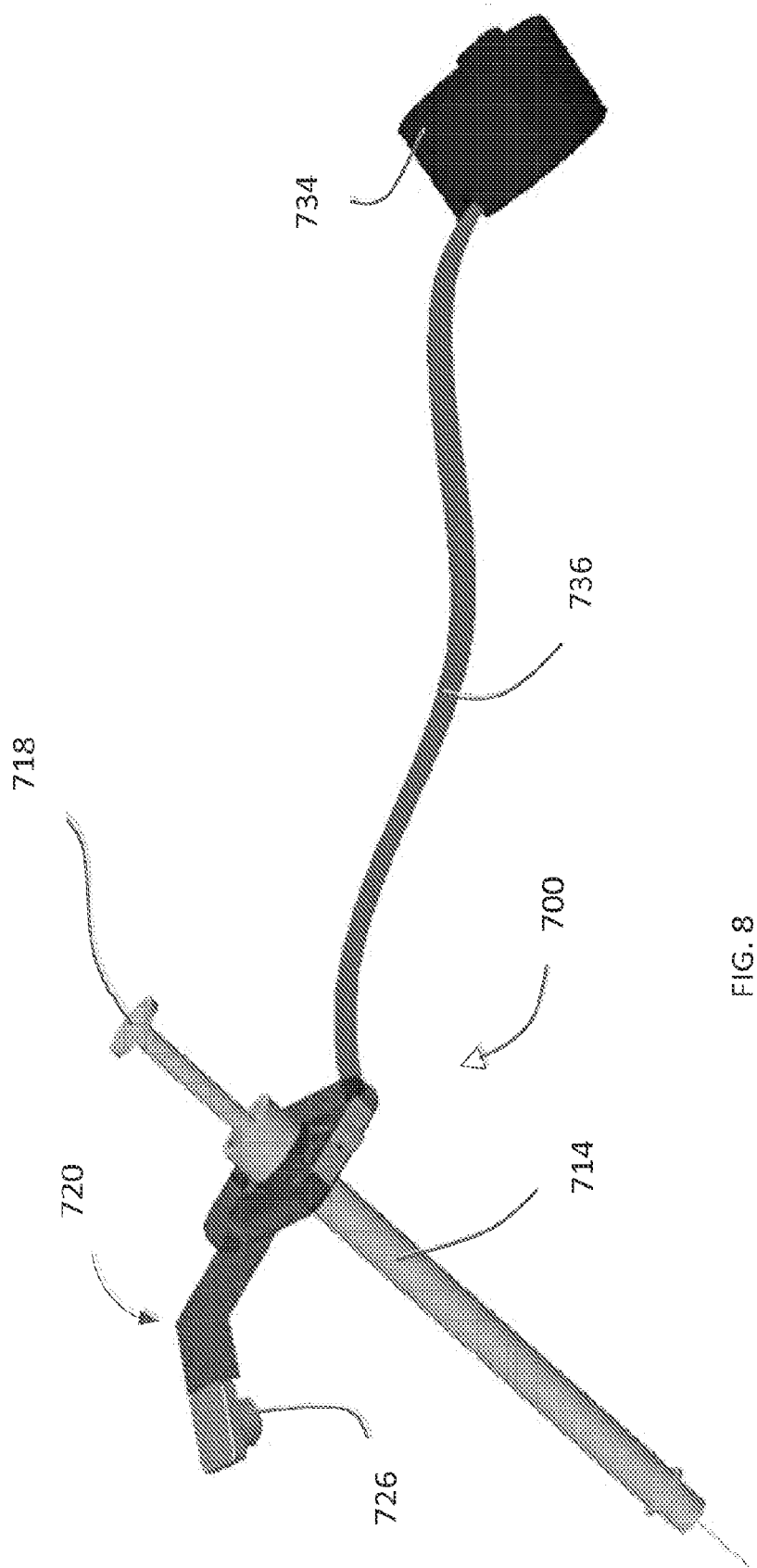
Figure 9A:
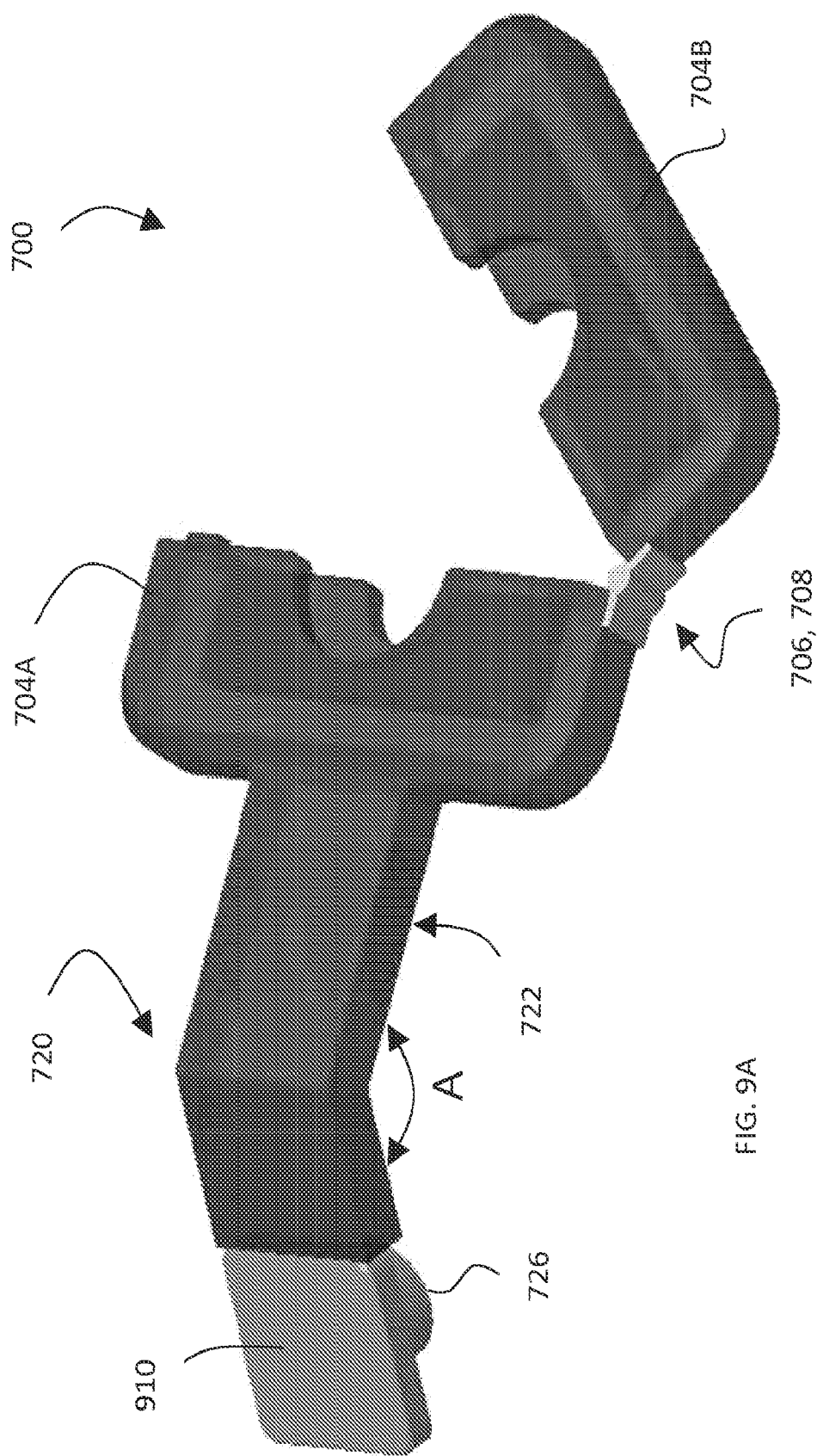

To this end, and in further reference to the drawings, FIGS. 7, 8, and 9A present different perspective views illustrating schematically an embodiment 700 of a monitoring system that includes a bracing element or bracer 704 (shown to contain two frame elements 704A, 704B repositionably affixed to one another about a pivotal point 706). In one implementation (and as shown), the two frame elements 704A, 704B of the bracer 704 have substantially similar structures and, as such, can be considered to be halves of the bracer 704. Generally, however, the bracer frame elements 704A, 704B may be structurally different but are configured to fixatedly and tightly accommodate a drug-container disposed between them. The bracer 704 is preferably equipped with a fastening means 710 disposed at the facing each other ends of the bracer frame elements 704A, 704B to facilitate a fixed cooperation therebetween after the elements 704A, 704B are swung towards one another about the pivotal point 706. FIGS. 7 and 8 illustrate the embodiment 700 in juxtaposition with a syringe 714 having a needle 716 and a plunger 718 and filled with liquid (fluid) drug, while FIG. 9A is a view of the embodiment 700 by itself, with the bracer frame elements 704A, 704B hingedly open about an axis passing through the pivotal point 706. In a specific implementation of the invention the cooperation between the frame elements 704A, 704B may be, optionally, completely detachable, in which case a second fastening means (not shown) is used in place of the hinge about the pivotal point 706.

In further reference to FIGS. 9A and 9B, the embodiment in which the second frame element 704B is adjustably and/or repositionably connected to the first frame element 704A with a hinge 708 as discussed. So connected, the frame portions 704A, 704B form a tool for attachment to the syringe 714 that is configured as a compound lever for grasping the syringe, a pincer of sorts. The first frame element 704A is solidly integrated with a mounting arm portion 720 that is structured to define a dihedral angle A. This angle A can range from about 60 to about 200 degrees, preferably from about 90 to about 170, and even more preferably from about 120 to about 150 degrees. In a specific implementation, the angle A is about 135° to facilitate an optimal viewing of the target portions of the syringe 714 by a camera of the embodiment, as is discussed below.

The mounting arm 720 carries a camera 726 on a surface 722, which surface faces (at the angle A) the brace frame element 704A. The camera 726 is optionally equipped with a micro-optical system including a lens. The mounting arm 720 may additionally carry at least one light source (not shown) on the surface 722, the light from which provides required illumination of a scene an image of which the camera 726 is enabled to capture. In one embodiment, the affixation of the camera 726 at mounting arm 720 can be effectuated with the use of an appropriate adhesive or an alternative mounting means know in the art (such as with the use of a threaded indentation or bore formed in the body of the arm 720). The light source(s) may include an LED, a halogen bulb, or another source of light having appropriate dimensions. When several light sources are employed in juxtaposition with the surface 722 of the arm 720, such light sources may be spatially distributed around the camera 726 in a pre-determined geometric fashion (for instance, circular, or polygonal depending on the number of the light sources). The spatial positioning and/or orientation of the camera 726 and the associated optional light source(s) is such that, in operation, when the syringe 714 is secured between the frame elements 704A, 804B, both the area around the needle 716 and a portion of the body of the syringe 814 that contains drug falls within the field-of-view (FOV) of the camera 726. So structured and dimensioned, the area of the tissue in which the needle is injected during the drug-administering session and a level of the drug in the container of the syringe 714 can be observed and video recorded, thereby providing data representing the compliance with the regimen or lack thereof. When light sources are used in conjunction with the camera, the level of irradiance provided by the light sources for the space within the FOV of the camera 726 is made sufficient to acquire informative images under conditions of ambient illumination.

In reference to FIG. 9B, an optional lens of the camera 726 preferably has a field of view of about 60 degrees to about 180 degrees (defined by a full linear angle). In one embodiment, for example, a wide angle lens with about 120 to about 180 degree field of view can be used, or, preferably, with the field of view from about 150 degrees to about 180 degrees. Generally, a wide angle lens is preferred to define a field-of-view that covers both the needle-injection area and a portion of the syringe tube that carrier scale marks used to determine the amount of drug injected from the syringe. In a related embodiment, the working distance between the camera 726 and the needle ranges, in operation, between about 40 mm to about 75 mm. Accordingly, the optional lens of the camera 726 has a focal length from about 0.2 mm to 4 mm, or more preferably from about 0.5 mm to about 2.54 mm, and most preferably from about 0.75 mm to about 1.5 mm. A lens' F-number may range from about 1 to about 5, or more preferably from about 1.5 to about 3. An image detector associated with the camera 726 (not shown and positioned, for example, behind the camera 726 in a camera-supporting portion 910 of the arm 720) is configured for acquisition of optical data representing the scene including the vicinity of the needle 716. (The camera-supporting portion 910 of the mounting arm 720 can be structured as an unmovable portion of the mounting arm as shown in FIG. 9B or, alternatively, as a portion that is movable and/or repositionable with respect to the rest of the mounting arm 520, as discussed below in reference to FIG. 11). In general, a CMOS based detector with size ranging within the range of about $\frac{1}{8}$"-$\frac{1}{2}$" and pixel count in a range of 400*400 to 2048*2048, or higher as becomes available preferably $\frac{1}{3}$", with a pixel count of about 1024*1024 is used, though other detectors may be employed in a related implementation. Additionally, an embodiment of the monitoring system may contain a user interface with a time-counting and/or sound- or light-emitting mechanism and/or wireless transmitter transmitting data to an external patient-readable device to remind the patient that it is time for their next injection to be administered. The action of turning on the embodiment and performing an injection or depressing a relevant trigger of the user interface could then stop or re-set such notification reminder (which may be configured as light alert, email or text to the patient's phone, or sound alert, for example, to name just a few).

Referring again to FIGS. 7 and 8, the camera 726 (and/or the optional light source(s) associated with the camera on the surface 722) are operably (at least electrically) connected with a base unit 734. The base unit 734 is configured as a holder for a power unit (such as an optionally replaceable and/or rechargeable battery) and/or auxiliary hardware (such as electronic circuitry and/or programmable processor and/or tangible storage medium) required for operation of the embodiment 700. As shown, the operable communication between the embodiment 700 and the base unit 734 may be established via a flexible cable 736. The base unit 734 may be cooperated with the camera 726 via an electrical connector passing along the frame elements 704A, 704B (whether internally or externally with respect to the frame elements) or, alternatively, the flexible cable 736 may be attached to the element 704A directly. In yet another implementation, the communication between the camera 726 and the base unit 734 may be structured as wireless.

In a related implementation, however (not shown), the base unit 734 may be absent and at least one of the power unit and the auxiliary hardware elements may be disposed within or in juxtaposition with the frame element 704A, 704B or arm 720. In an embodiment devoid of base unit 734 (not shown), the operable, data- and energy-transfer enabled connection between the camera 726 and the external battery and/or data storage medium is configured either through a direct wire-based connection or wirelessly (with the use of Bluetooth, intranet, or internet based communication means).

Optionally, the base unit 734 is equipped with a port (not shown) adapted for operable connection with a computer or another external electronic device (not shown) in a fashion similar to that of an USB port, for example, or an electrical plug. The optional port is configured for transfer of data and/or power between the external device and the base unit 734 (for example, to recharge a battery within the base unit 734 or to transfer the data collected by the system 700 to the external electronic device). In a related implementation, the port of the base unit 734 may be adapted to facilitate spatial docking of the system 700 at an external electronic platform. Such docking platform can allow for charging and data transfer, weighting or such other functions as are found to be beneficial.

Referring now to FIGS. 10A, 10B, 10C, and 10D, and in further reference to FIG. 7, an example of structure of the bracer frame element 704B is depicted. To accommodate a typical syringe 714 between the bracer frame elements 704A, 704B in operation, a single bracer frame element 704B includes a substantially solid shell 1010 having a wall that defines an inner volume 1012 dimensioned to fixatedly accommodate a rim or collar (flange) of the syringe 714 positioned between the frame elements 704A, 704B when then fastening means 710 is closed. Accordingly, the wall 1010 may be shaped to define semicircular curved portions 1020, 1022 of the perimeter of the wall 1010 along a facet of the frame element 704B that is facing the reciprocal frame element 704A. In a specific case where the frame elements 704A, 704B are dimensioned to be halves of the bracer 704, the element 704A is structured in a substantially similar fashion. Here, each of the semicircular portions 1020, 1022 of each of the elements 704A, 704B defines a corresponding semicircular cradle dimensioned to accommodate a substantially cylindrically-shaped object such that, when the bracer frame elements 704A, 704B are brought together and fastened with the fastening means 710 (see, for example, FIG. 7), these cradles merge to define a circular brace dimensioned to clasp and lock the syringe (or another quasi-cylindrical object) disposed substantially perpendicularly to a common plane defined by the frame portions 704A, 704B.

Figure 11:
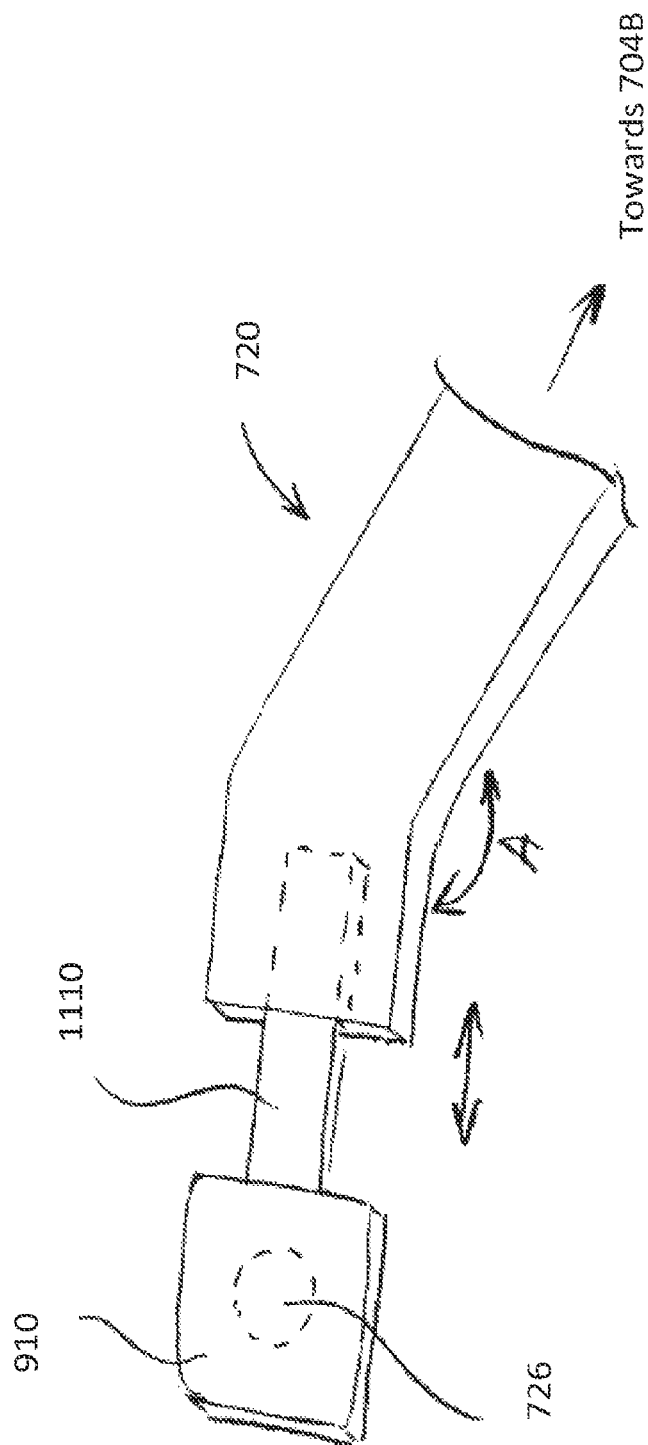
FIG. 11 is a diagram illustrating an optionally spatially-expandable component of the embodiments of FIGS. 1A, 1B, 2, 3, 4A, 4B, 5A, 5B, 7, and 8.
Figure 12:
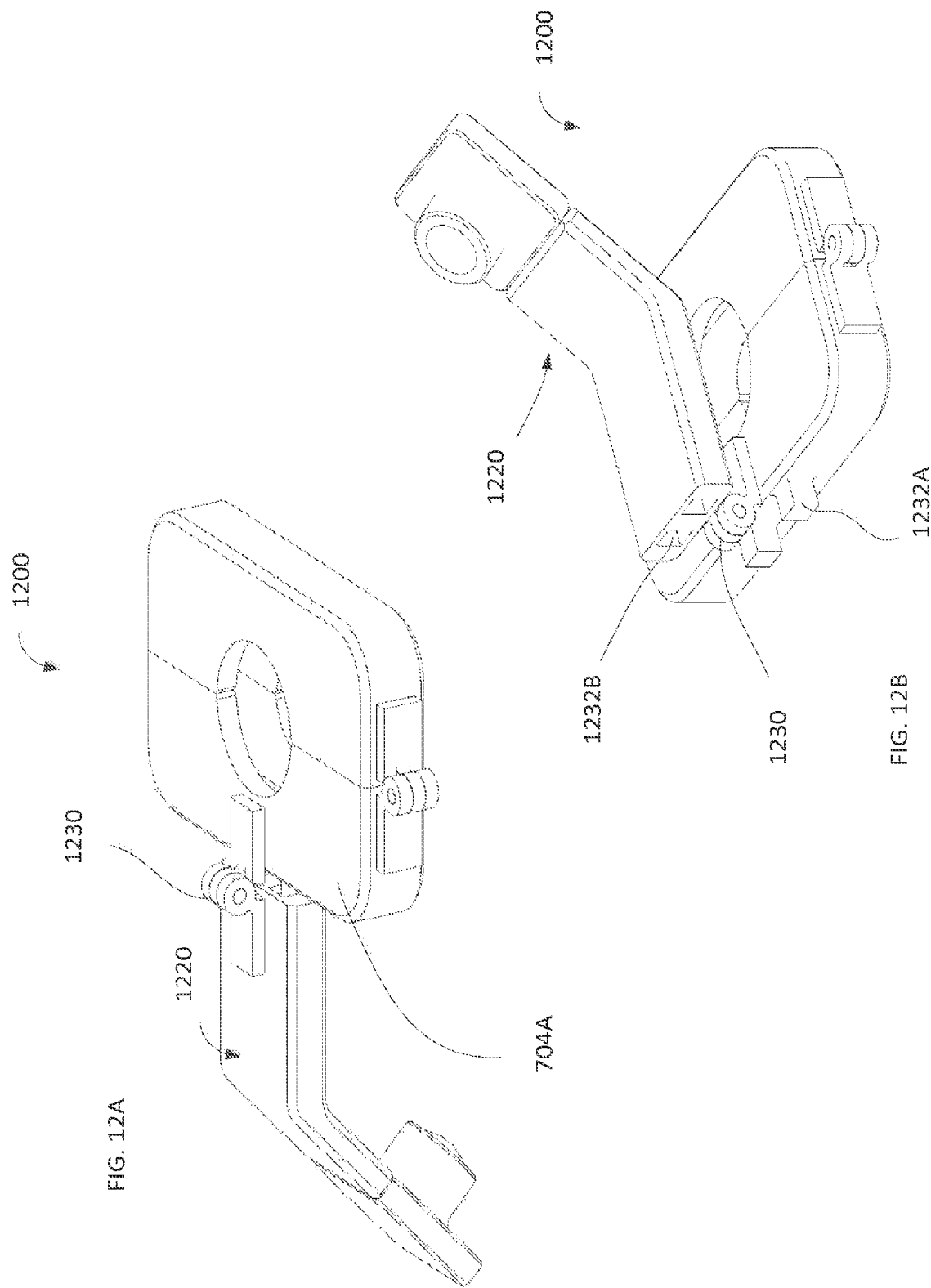
FIGS. 12A, 12B are additional illustrations of the embodiment of FIGS. 7, 8.

Modifications to, and variations of, the illustrated implementations may be made without departing from the inventive concepts disclosed herein. For example, the mounting arm 720 may include two sub-portions that are movable with respect to one another. For example, a portion of the mounting arm 720 that contains the camera 726 (shown as the portion 910) may be structured to be controllably slidable with respect to the rest of the mounting arm such as to enable modification of the distance separating the camera 726 from the frame element 704A. To this end, as shown in FIG. 11, the arm 720 includes a hollow appropriately dimensioned to accommodate a piston 1110 (of the movable sub-portion of the arm 720) therein. To facilitate the lengthening or shortening of the mounting arm 720, the piston 1110 can be moved out (extended) from the hollow of the arm 720, in a step-wise and/or continuous fashion, or pushed in to the hollow (retracted, in a telescopic fashion for example). In a related and/or alternative implementation, shown as 1200 in FIGS. 12A, 12B, the mounting arm 1220 may be attached to the frame element 1204A with the use of a turnably-affixing means (shown, in the specific example of this embodiment, as a hinge 1230). In a folded configuration (of FIG. 12B, when the mounting arm 1220 is turned about the hinge towards the bracer 704) the overall linear extent of the embodiment is reduced, which facilitates storage and handling of the device of the invention. To facilitate support of the mounting arm 1220 in an unfolded position, one or more fixators 1232A (shown in FIG. 12B as extensions or protrusions defined with respect to the bracer 704) can be implemented on a surface of the frame element 704A, which fixators operably cooperate with one or more of corresponding pockets 1232B defined in the body of the mounting arm 1220. The fixator(s) 1232A and the pockets 1232B may have any cross-sectional profile such as, for example, rectangular as shown or cylindrical. Such alternative configuration enables controllable repositioning of the mounting arm 1220 with respect to the bracer 704 so as to fold the arm 1220 back over the bracer frame elements.

Figure 13:
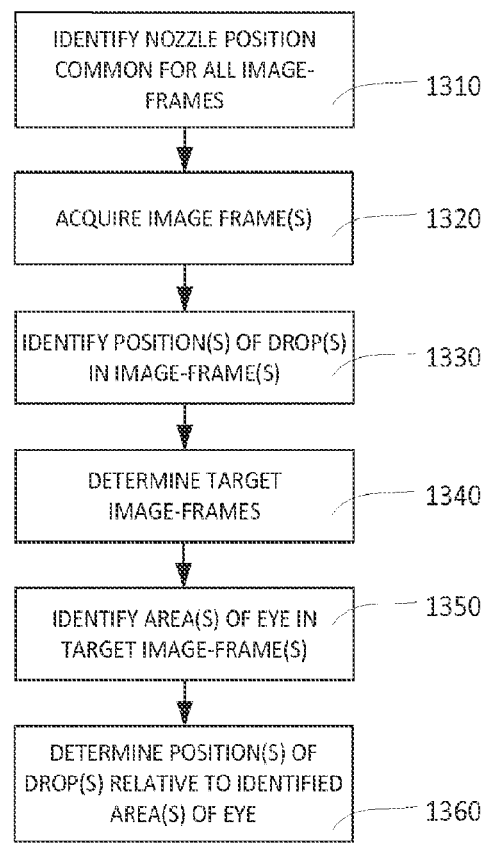
FIG. 13 is a flow-chart of an algorithm of the invention.
Figure 14:
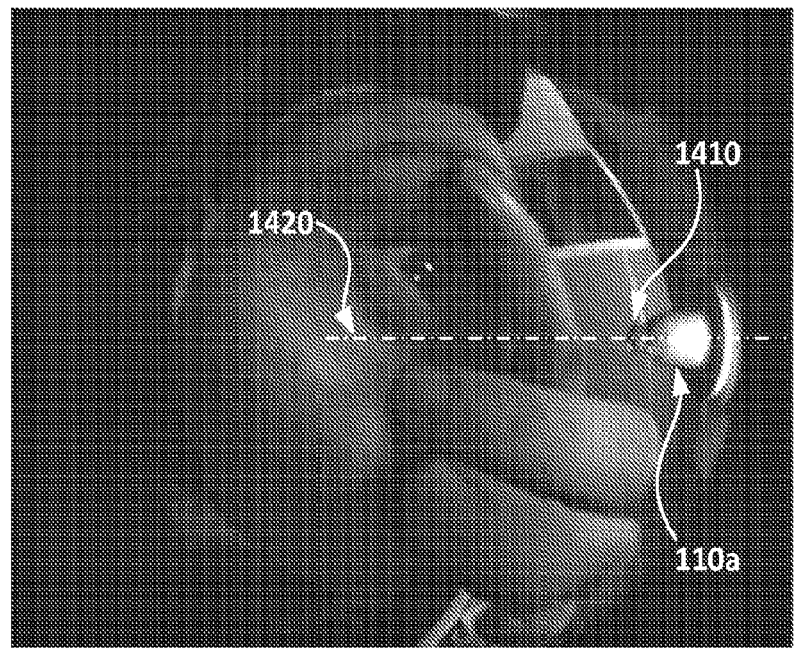
FIG. 14 is a gray image acquired during the eye-drop delivery procedure with an embodiments of the invention and illustration a position of the nozzle, of a drop-container fixed in the embodiment, with respect to the field-of-view of the camera of the embodiment.

FIG. 13 schematically presents a flow-chart of an algorithm to allow full or partial automation of the reading of the images from the invention directed to a determination of whether the delivery of drug to an eye, with the use of the device of the invention (such as that of the embodiment 100). Such a determination can be done at a reading center, by a software program, and/or a combination of the two. The determination is rooted in the analyses of image-frames (video-frames) of the recording (of the process of drug-delivery) made with the use of the camera of the embodiment. In reference to FIGS. 1, 5, 13, and 14, after the container 110 is inserted into the container-holder 500 and the angular deviation a between the first and second frame components 101, 102 is chosen, the relative position of the nozzle 110a with respect to the camera 106 is fixed and, therefore, the position of the nozzle 110a in the field-of-view (FOV) of the camera 106 remains substantially constant for all image/video frames. The identification of the nozzle position in a frame's FOV at step 1310, therefore, simplifies the search for an image of a drop of the drug in a FOV of a given frame (see FIG. 14), because the image 1410 of a drop is located in an area that is smaller than the overall area of the FOV and on a line 1420 associated with the axis of the nozzle 110a. Accordingly, a template or image of the nozzle 110a derived from an image frame can be used to correlate with the red, green, and/or blue (R, G, or B) components of a gray image of a frame to find the position, in the image, corresponding to the maximum correlation value (which image location also corresponds to the image location of the dropper nozzle.

The correlation figure of merit, defined between a given image frame and an image or template of the nozzle and showing the degree of similarity between the nozzle template and an image frame is given by Eq. (1) as $$\text{Cor}(x, y) = \frac{\sum_i \sum_j [T(i, j) - \overline{T}][F(i+x, j+y) - \overline{F}(x, y)]}{\left\{ \sum_i \sum_j [T(i \cdot j) - \overline{T}]^2 \cdot \sum_i \sum_j [F(i+x, j+y) - \overline{F}(x, y)]^2 \right\}^{1/2}}, \quad (1)$$

where T(i, j) is the irradiance value corresponding to a pixel value of the nozzle template, and F(i, j) is the pixel value of the gray image corresponding to a given image-frame. $\overline{T}$ is the average, over the nozzle template, of the pixel irradiance values and $\overline{F}(x, y)$ is the average of the pixel irradiance values of local image area which is the function of position (x,y). Cor(x, y) is the correlation coefficient at position (x, y). Because the overall image area in which the image of the nozzle is located is generally known, the calculation of the correlation coefficient facilitates defining of the exact, precise position of the image of the nozzle in the given image frame, thereby saving calculation time.

After the position of the nozzle in the image-frame is identified, the area of the image associated with a drop delivery can be determined and compared with the ROI of the patient's body (such as a patient's eye) designated as a target for the drop delivery. The area of the image associated with a drop delivery referred to as an "image area of drop delivery" hereinafter, is defined as an area of the image extending from the positional of the nozzle along the central line 1420 and limited by geometric boundaries determined as a function of the field of view of the imaging lens and the pixel size of the detectors of the imaging camera. For example, for a FOV of about 170 degrees and the pixel size of about 10 microns, the image area of drop delivery is about 50 pixels wide by 120 pixels long. The steps of the algorithm discussed below are referring to the search of a drop only inside this area of the image.

Figure 15:
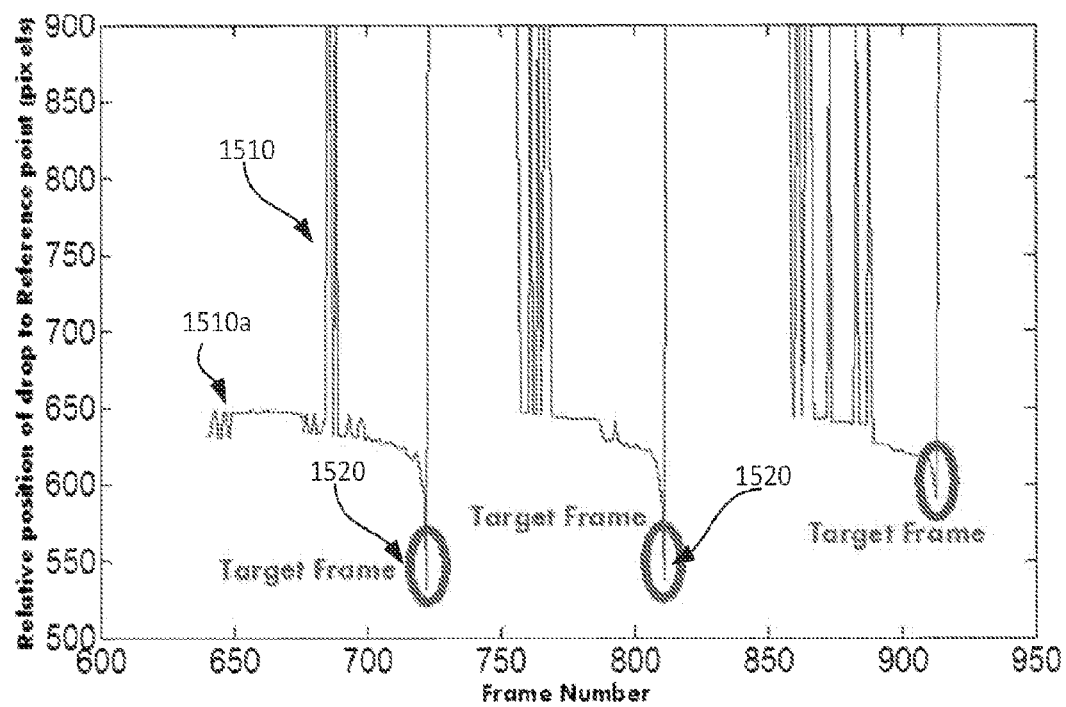
FIG. 15 is a plot showing a change in a position of eye-drop(s) as a function of a image/video-frame number.

The detection of a drop in a given image frame is based on detection of the highest value of intensity of light from the at least one light source 107 of the embodiment that has been reflected by the drop emitted through the nozzle 110a and captured in a given image within the image area of drop delivery. By determining the locations of these local maxima of intensity, a position of a drop in the image can be identified, at step 1330, for each of the image frame that has been acquired at a step 1320. In one example, the position of a drop can be determined by averaging the positions of multiple local maxima to obtain a better estimate. Further, by analyzing the drop position in several sequentially acquired image frames, the moving direction and path of a drop can be predicted as well. The overall dependence of position(s) of a given drop of drug emitted from the nozzle 110a vs. frame number can be obtained (as shown in the example of curve 1510 of FIG. 15). When the drop position value appears noisy (1510a), it means that the drop is growing in size; however when its position changes sharply, it means that the drop is separated from the nozzle 110a and falling towards the eye. From the curve such as curve 1510, the target frames (corresponding to frames encircled as 1520 in FIG. 15) which we are interested, are determined at step 1340. The target image frames correspond to the frames recorded during the duration of time between a moment of drop's separating from the nozzle and a moment of drop's landing into or next to an eye According to the sequence of image/video frames of the recording, the area of the eye can be defined using color information contained in the image sequence (based, for example, on differences between the color of an eyeball and the color of the skin of the face). The identification of the area of the eye, Eye(x,y), can be performed, for example, based on the considerations of Eq. (2) and color segmentation of a given image-frame:

$$\text{Eye}(x, y) = \begin{cases} 1 & \text{(values of } R, G, B \text{ are exceeding a chosen threshold)} \\ 0 & \text{(values of any of } R, G, B \text{ is below the chosen threshold)} \end{cases} \quad (2)$$

In one implementation, the color segmentation—and, in particular, the identification of the eyeball area in every image frame—is based on recognition that the color gamut of the eye-ball area is rather close to white, while the rest of the image is substantially darker. Accordingly, by setting the appropriate thresholds for R, G, and B channels based on such consideration, the eye-area can be safely identified in every image frame.

Figure 16A:
FIGS. 16A, 16B are images illustrating, respectively, a step of color segmentation of an image-frame and the resulting image with an area of the eye identified according to an embodiment of the invention.
Figure 16B:
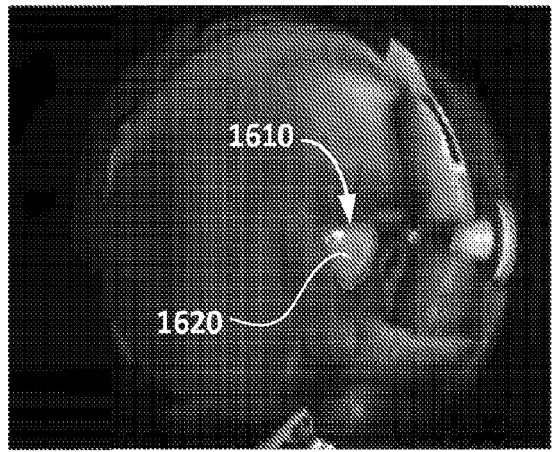

In addition, because the embodiment of the monitoring device of the invention typically employs a wide angle lens (full FOV of about 170 degrees), in most of practical cases the eye area is located, in the image frame, in the central part of the field of view. This consideration also facilitates and simplifies the image identification process. That means we can only search the eye area in the central part and this can also save the calculation. FIGS. 16A and 16B illustrate step 1350 of the algorithm 1300, at which the determination of the eye area (bound by a closed boundary) is performed (and optionally including the sub-steps of color segmentation and determination of an edge 1610 of the eye area 1620).

Figure 17:
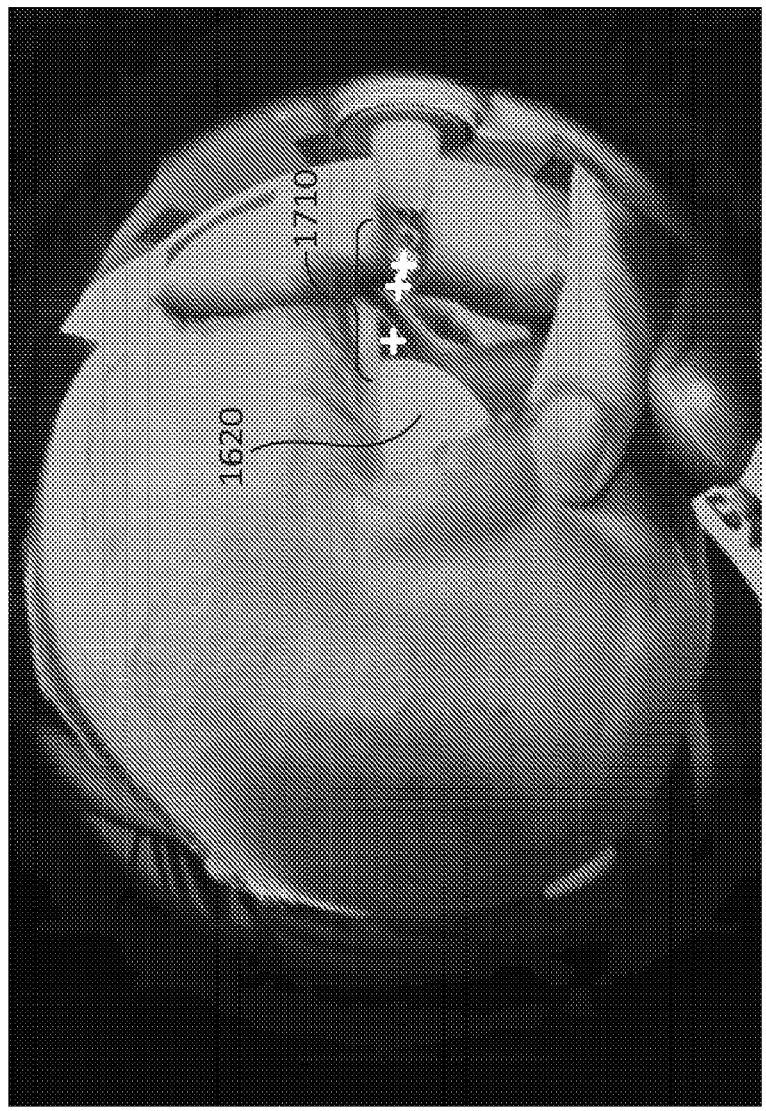
FIG. 17 is a compilation of several video-frames with over-imposed markers showing the trajectory of an eye-drop from the nozzle of the drop-container towards the eye.

The determination of whether a drop emitted from the nozzle 110a reached the eye area (i.e., was "on target") is made at step 1360, of FIG. 13, based on the image data representing a drop path (from the target frames) and the edge 1610 of the eye area. FIG. 17 shows the image fusion (overlap of images) of 5 frames from the vicinity of the target frame, which fused image clearly shows the track of a drop (marked with crosses 1710) on its way to the eye area 1620. As a result of the determination, an identifier—such as a software flag "yes" or "no", or other recordation or mark—can be generated and stored by the system for future assessment of the success of the patient-implemented drug-delivery process and compliance with the regimen. Knowing at least some of the positions 1710 of the drop determine from the video-recording, the user can predict the path of a drop even before the drop's landing into the eye or outside of the eye.

Disclosed aspects of the invention, or portions of these aspects, may be combined in ways not listed above. For example, the recording means can be operably connected to a storage medium to store videos and transfer them for processing in multiple formats including .mpeg, .flv, .mov, .movie .rm, .wmv, and other similar or new formats that are developed. In one embodiment, the device can be used to image delivery of a syringe injection, ear drops, nose drops, and or other drops to skin and/or such other tissue. This may aid individuals in correctly administering the eye drops. In one embodiment, the system is additionally equipped with image analysis software which can independently assess all image-frames acquired during the drug delivery application procedure and determine the time of application as well as how much of the drug was actually delivered to the desired tissue (accurate assessment of volume of medication that was applied to a delivery site). In another embodiment, an external monitor is utilized to present real-time video of the eye and the space proximal to the eye during eye drop administration. The monitor may be equipped with an infrared heat detection system to provide a more detailed visualization of exactly how much medication was dispensed and how much of it reached the target tissue. In some embodiments, the device shall be attachable to an optional stabilizing device. This stabilizing device may be a band that goes around the patients head, a brace, or any device that stabilizes the video recording device, such as gyroscopic systems. In some embodiments, the stabilizing device shall permit the patient to have both their hands free for administering the eye drop(s). The stabilizing device shall also make the recording clearer as some patients have shaky hands and/or some patients will inadvertently move the eye drop device while administering the eye drops due to the pressure needed to cause release of the eye drops. In some embodiments, the device may contain an automated mechanical or other way to compress the drug-container for controlled delivery of the drop without the need to squeeze it. In some embodiments of the invention the device will contain a clock so as to allow time stamping of the videos, and the exact time the drops were taken. In some embodiments the clock can also notify the patient by sound, light, vibration, email and/or any other such mechanism when it is time to take the next dose of the medication.

Accordingly, the invention should not be viewed as being limited to the disclosed embodiment(s).

What is claimed:

1. A method for monitoring a patient-performed drug delivery from a hand-held container to a region of interest (ROI) associated with the patient's body, the method comprising:
    applying hand input to a drug-delivery system to squeeze a drop of a drug from a tip of the container and to release said drop from said tip,
        the drug-delivery system including the container containing said drug and a container-holding system having a first frame component structured to house the container therein along an axis thereof and a second frame component extending from the first frame component,
        the second frame component carrying an imaging camera having an optical field-of-view (FOV), an optical detector, and configured to record images of a scene within the FOV,
        the FOV covering the tip, the ROI, and a space separating the tip from the ROI;
    recording a series of image frames, each frame representing a corresponding position of said drop in said space; and
    producing a report representing whether said drop landed in, partially in, or out of the ROI,
        wherein the producing includes determining target image frames from the series, said target image frames represent only an advancement of said drop through said space.

2. A method according to claim 1, wherein the hand-held container includes a squeezable bottle and the ROI includes a patient's eye.

3. A method according to claim 1, wherein the producing includes producing a report based at least on a correlating figure of merit calculated in reference to an image frame and a template containing an image of the tip.

4. A method according to claim 1, wherein the producing includes identifying a position of the tip that is common for all image frames from the series.

5. A method according to claim 1, further comprising identifying a closed boundary of the ROI in a target image frame, from the series, based on color segmentation of an image contained in said target image frame.

6. A method according to claim 1, further comprising determining a position of said drop relative to the ROI based at least on the FOV and a size of a pixel of the optical detector.

7. A method according to claim 1, wherein the second frame component includes a source of radiation facing the scene, and further comprising illuminating said drop with said source of radiation for the recording of each image frame from the series.

8. A method according to claim 7, wherein the source of radiation includes a source of visible light.

9. A method according to claim 1, wherein the recording includes recording a series of image frames in IR light.

10. A method according to claim 1, wherein the producing includes generating an identifier representing whether said drop landed in, partially in, or out of the ROI based at least on a correlation figure of merit calculated according to $$Cor(x, y) = \frac{\sum_i \sum_j [T(i, j) - \overline{T}][F(i+x, j+y) - \overline{F}(x, y)]}{\left\{\sum_i \sum_j [T(i \cdot j) - \overline{T}]^2 \cdot \sum_i \sum_j [F(i+x, j+y) - \overline{F}(x, y)]^2\right\}^{1/2}},$$

wherein T (i, j) is an irradiance value corresponding to a pixel of the template, F(i j) is a pixel irradiance value of the image frame, $\overline{T}$ is an average of pixel irradiance values calculated over the template, and $\overline{F}(x, y)$ is an average of the pixel irradiance values of a local image area of the image frame.

11. An article of manufacture comprising:
a mount dimensioned to secure a chosen fluid container having a tip,
the mount having first and second frame components and containing a ring-like adapter structured to ensure that said fluid container is secured in a portion associated with a neck of said fluid container,
the first frame component including first and second ends,
the second frame component connected to the first frame component at an angle,
the second frame component carrying (i) a lens with a field-of-view (FOV) that covers a vicinity of the tip once the fluid container is secured in the mount and (ii) an optical detector;
wherein the optical detector is disposed to receive, from the lens, an irradiance distribution corresponding to light received from an area in the vicinity of the tip, and
wherein said adapter is configured to accommodate fluid containers of variable sizes and shapes.

12. An article according to claim 11, wherein the first frame component has a length that is adjustable along the fluid container that has been secured in the mount.

13. An article according to claim 11, further comprising a source of light disposed on the second frame component to illuminate the area in the vicinity of the tip.

14. An article according to claim 11, wherein the angle is adjustable, with a hinge operably connecting the first and second frame components, between about 0 degrees and 270 degrees.

15. An article according to claim 11, wherein the angle is fixed.

16. An article according to claim 1, wherein the ring-like adapter is structured to secure said fluid container removably.

17. An article according to claim 11, further comprising a video-recording means in operable communication with said optical detector.

18. An article according to claim 11, wherein, when (i) the hand-held container includes a squeezable bottle filled with a drug to be delivered to a patient's eye and (ii) said bottle is secured in the mount and squeezed by the patient to form a drop of the drug at the tip and to effectuate such a delivery,
the area in the vicinity includes the tip, the patient's eye, and a space separating said tip and said eye,
and further comprising:
electronic data-processing circuitry in operable communication with said optical detector, said circuitry programmed to record and process said received optical data to determine temporal and spatial characteristics of the area in the vicinity of the tip; and
a tangible, non-transitory storage medium with program code stored thereon which, when the program code is executed by the electronic data-processing circuitry, causes said circuitry to:
record a series of image frames, each frame representing a corresponding position of said drop in said space; and
generate an identifier of said spatial and temporal characteristics based at least on a correlation figure of merit calculated in reference to an image frame and a template containing an image of the tip.

19. An article according to claim 18, wherein said spatial and temporal characteristics represent one or more of (i) a merit of success of delivery of the drug to the patient's eye, (ii) a first value associated with an amount of drug dispensed from the hand-held container, (iii) a second value representing time of drug delivery; and (iv) a third value representing a proportion of the first value delivered to the patient's eye.

20. An article according to claim 11, further comprising a stabilizing device operable, in conjunction with the hand-held container, to compensate for tremor in a hand of a patient operating the article to deliver of a fluid from the container to the patient's eye.

* * * * *